(12) United States Patent
Levy et al.

(10) Patent No.: US 6,333,194 B1
(45) Date of Patent: Dec. 25, 2001

(54) HYDROGEL COMPOSITIONS FOR CONTROLLED DELIVERY OF VIRUS VECTORS AND METHODS OF USE THEREOF

(75) Inventors: Robert J. Levy, Merion Station; Timothy Crombleholme, Haverford, both of PA (US); Narendra Vyavahare, Erial, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 09/487,854

(22) Filed: Jan. 19, 2000

Related U.S. Application Data

(60) Provisional application No. 60/116,538, filed on Jan. 19, 1999.

(51) Int. Cl.[7] .............................. C12N 15/63; C12Q 1/68; A61K 51/00; C08B 37/04; C07H 21/02
(52) U.S. Cl. .............................. 435/450; 435/6; 424/1.25; 424/1.33; 424/1.53; 424/497; 536/3; 536/23.1
(58) Field of Search .................................. 514/44; 435/6, 435/69.1, 91.1, 455, 458; 536/23.1, 24.5, 3; 424/1.25, 1.33, 1.53, 497

(56) References Cited

U.S. PATENT DOCUMENTS

| | | |
|---|---|---|
| 4,004,979 | 1/1977 | Avrameas et al. . |
| 4,452,892 | 6/1984 | Rosevear . |
| 4,647,536 | 3/1987 | Mosbach et al. . |
| 5,034,506 | 7/1991 | Summerton et al. . |
| 5,529,777 | 6/1996 | Andrianov et al. . |
| 5,616,487 | 4/1997 | Palsson et al. . |
| 5,646,032 * | 7/1997 | Ter Muelen et al. ................. 435/6 |
| 5,648,252 | 7/1997 | Dumitriu et al. . |
| 5,851,521 | 12/1998 | Branellec et al. . |
| 5,869,230 | 2/1999 | Sukhatme . |
| 5,879,713 | 3/1999 | Roth et al. . |
| 5,885,829 | 3/1999 | Mooney et al. . |
| 5,945,100 * | 8/1999 | Fick ................................ 514/44 |
| 6,027,892 | 2/2000 | Chang . |

OTHER PUBLICATIONS

Schofield et al. Brit. Med. Bull., vol. 51, No. 1, pp. 56–71, 1995.*
Friedmann, T. Scientific American, Jun. vol., pp. 96–101, 1997.*
Crystal, R.G. Science, vol. 210, pp. 404–410, 1995.*
Orkin et al. Report and Recommendations of the Panel to Assess the NIH Investment in Research on Gene Therapy, 1995.*
Branch, A. Trends in Biochem. Sci., vol. 23, pp. 45–50, 1997.*
Crooke, S.T. Antisense Research and Application, chapter 1, pp. 1–50, Published by Springer–Verlag, 1997.*
Jolly, D. Cancer Gene Therapy, vol. 1, No. 1, pp. 51–64, 1994.*
Bello et al., 1985, J. Biomol. Struct. Dyn. 2:899–913.
Cox, D.A., 1995, Cell Biology International 19: 357–371.
Fang et al., 1996, Proc. Natl. Acad. Sci. USA 93:5753–5758.
Feldman et al., 1997, Gene Therapy 4:189–198.
Feldman et al., 1997, Cardiovasc. Res. 35:391–404.
Flake et al., 1996, N. Engl. J. Med. 335:1806–1810.
Igel et al., Jul., 1996, Diabetologia 39:758–765.
March et al., 1995, Hum. Gene Therap. 6:41–53.
Martinez–Fong et al., 1994, Hepatology 20:1602–1608.
Moser et al., 1996, Vaccine 14:1235–1238.
Nabel et al., 1995, Gene Ther. Cardiovasc. Dis. 91:541–548.
Nielsen et al., 1991, Science 254:1497.
Roth et al., 1997, J. Natl. Cancer Inst. 89:21–39.
Schneider et al., 1990, Tetrahedron Lett: 31:335.
Slavin, 1995, Cell Biol. Intl. 19:431–444.
Smith et al., 1996, Gene Ther. 3:190–200.
Tripathy et al., 1996, Nat. Med. 2:545–549.
Tzimagiorgis et al., 1996, Nucl. Acids 24:3476–3477.
Uhlmann et al., 1990, Chem. Rev. 90:543–584.
Van Belle et al., 1998, Hum. Gene Ther. 9:1013–1024.

* cited by examiner

*Primary Examiner*—Andrew Wang
*Assistant Examiner*—Jane Zara
(74) *Attorney, Agent, or Firm*—Foley & Lardner

(57) ABSTRACT

The invention relates to compositions and methods for delivering a virus vector to an animal. The compositions include compositions which comprise a hydrogel matrix (e.g. a collagen matrix which can comprise a poloxamer or an alginate) containing a virus vector therein in a transfectious form. The invention also includes methods of making such hydrogel precursor mixtures and hydrogel matrices, including particles, devices, bulk materials, and other objects which comprise, consist of, or are coated with such mixtures or matrices. The invention further relates to compositions comprising a hydrogel precursor mixture having a virus vector suspended therein, which, when administered to an animal, gel to form a hydrogel matrix containing a virus vector therein in a transfectious form. Methods of delivering a virus vector to an animal tissue are also described.

34 Claims, 3 Drawing Sheets

Hydrogel and Adv-LacZ 5X

Adv-LacZ injection

Hydrogel and Adv-lacZ 10X

HYDROGEL COMPOSITIONS FOR CONTROLLED DELIVERY OF VIRUS VECTORS AND METHODS OF USE THEREOF

CROSS-REFERENCE TO RELATED APPLICATIONS

This application is entitled to priority pursuant to 35 U.S.C. §119(e) to U.S. provisional patent application 60/116,538, which was filed on Jan. 19, 1999.

STATEMENT REGARDING FEDERALLY SUPPORTED RESEARCH AND DEVELOPMENT

This research was supported in part by U.S. Government funds (National Heart Lung and Blood Institute grant number HL38118), and the U.S. Government may therefore have certain rights in the invention.

BACKGROUND OF THE INVENTION

Gene therapy is generally understood to refer to techniques designed to deliver nucleic acids, including antisense DNA and RNA, ribozymes, viral genome fragments and functionally active therapeutic genes into targeted cells (Culver, 1994, *Gene Therapy: A Handbook for Physicians*, Mary Ann Liebert, Inc., New York, N.Y.). Such nucleic acids can themselves be therapeutic, as for example antisense DNAs that inhibit mRNA translation, or they can encode, for example, therapeutic proteins that promote, inhibit, augment, or replace cellular functions.

A serious shortcoming of current gene therapy strategies, including both ex vivo and in vivo gene therapy methods, is the inability of present vector and delivery system combinations to deliver nucleic acids efficiently into the interior of cells of a targeted population. In December, 1995, the U.S. National Institutes of Health issued a "Report and Recommendations of the Panel to Assess the NIH Investment in Research on Gene Therapy" (Orkin et al., 1995, National Institutes of Health, Bethesda, Md.). In this Report, it was recognized that the development of gene therapy approaches to disease treatment was being inhibited, in part, by a dearth of effective gene transfer vectors. The Report recognized a need for further research applied to improving vectors for gene delivery.

Virus vectors are generally regarded as the most efficient nucleic acid delivery vectors. Recombinant replication-defective virus vectors have been used to transduce (i.e., infect or transfect) animal cells both in vitro and in vivo. Such vectors have included retrovirus, adenovirus, adeno-associated virus vectors, and herpesvirus vectors. Although they are highly efficient for gene transfer, a major disadvantage associated with the use of virus vectors is the inability of many virus vectors to infect non-dividing cells. Another serious problem associated with the use of virus gene vectors is the potential for such vectors to induce an immune response in a patient to whom they are administered. Such an immune response limits the effectiveness of the virus vector, since the patient's immune system rapidly clears the vector upon repeated or sustained administration of the vector. Furthermore, insertion of a gene into the genome of a cell by a virus vector can induce undesirable mutations in the cell. Other problems associated with virus gene vectors include inability to appropriately regulate gene expression over time in transfected cells, toxicity and other side effects caused by delivery of virus vectors to human tissues (e.g. liver damage and myocarditis), and potential production and transmission to other humans of harmful virus particles.

Furthermore, virus gene vectors, as used in prior art methods, have the drawback that they often cannot be delivered to a selected tissue in a specific, localized manner. Instead, many prior art methods of administering virus vectors result in vector being dispersed systemically or to tissues which adjoin, or are in fluid communication with, the desired target tissue. The inability of such methods to localize virus vector reduces the utility of the methods, because non-localized virus vector can transfect unintended tissues, elicit immune responses, be rapidly excreted from the body, or otherwise suffer diminished transfection ability. A significant need exists for methods of delivering virus vectors in a localized manner.

Virus vectors are able, to a limited degree, to deliver proteins and other therapeutic molecules to the cells which the virus vectors transfect. Such proteins and other therapeutic molecules can be incorporated passively and non-specifically into virus vector particles. Alternatively, as is known in the art, certain virus vectors specifically incorporate fusion proteins comprising a protein having a polypeptide viral packaging signal fused therewith.

Even though virus vectors have been widely used in experimental gene therapy protocols and human studies (Feldman et al., 1997, Cardiovasc. Res. 35:391–404; Roth et al., 1997, J. Natl. Cancer Inst. 89:21–39), none of these vectors has proven efficacious for virus vector-mediated gene therapy. It has been hypothesized that the shortcomings of adenovirus vectors has been due, at least in part, to limited transgene expression resulting from the immune response of the host individual and to cytotoxic effects which the vectors have exhibited toward organs of the host individual (Smith et al., 1996, Gene Ther. 3:190–200; Tripathy et al., 1996, Nat. Med. 2:545–549; Nabel et al., 1995, Gene Ther. Cardiovasc. Dis. 91:541–548). Others working in the field have concentrated their efforts on mutating adenovirus vectors to render them relatively less immunogenic and toxic.

In addition to the low efficiency of virus vector uptake exhibited by most cell types and low levels of expression of the gene constructs delivered by virus vectors, many targeted cell populations are found in such low numbers in the body that the efficiency of transfection of these specific cell types is even further diminished. A critical need remains for gene therapy methods which can efficiently deliver virus vectors to targeted cell populations. Others working in the field have concentrated on attempting to specifically target adenovirus vectors to a particular cell type, for example by attaching a specialized receptor ligand to the vectors (Tzimagiorgis et al., 1996, Nucl. Acids 24:3476–3477).

A virus vector useful for gene delivery must be delivered to its target cells in a form in which the biochemical components of the virus retain their function. That is, the virus vector must retain the capacity to bind to target cells, to transfer a nucleic acid carried by the vector into the interior of the cell, and, in some circumstances, to catalyze chemical reactions involving that nucleic acid within the cell (e.g. reverse transcription, integration into the host cell genome, or promoting transcription of gene elements on the nucleic acid). Thus, it is important that the delivery vehicle by means of which the virus vector is administered to a patient not subject the vector to chemically harsh or biochemically inactivating conditions. Thus, many matrices are not compatible for contacting with virus vectors. Ideally, a matrix in or on which a virus vector is disposed should be biodegradable, and in a form which is amenable to use in relevant surgical and therapeutic interventions. Further complicating matters, the following physiological phenomena are some of those which can inhibit administration of a virus vector to an animal tissue.

Inability of the virus vector to interact specifically with cells of the desired tissue attributable to proteolytic degradation of one or more components of the virus vector by an enzyme in the animal.

Complexing of animal proteins or other molecules with one or more components of the virus vector, with the result that the virus vector is unable to interact specifically with cells of the desired tissue.

Sequestration of the virus vector in undesired tissues or organs of the animal (e.g. removal of virus vectors from the bloodstream by the liver).

Complications (e.g. immune reactions, inappropriate transfection, rapid clearance of vector from the subject, etc.) arising from non-localized delivery of the virus vector.

Inability of the virus vector to cross a physical barrier (e.g. the blood-brain barrier or peritoneal membranes) which separates the desired tissue from the site of administration of the virus vector.

Induction of an immune response in the animal which results in production in the animal of cells and proteins (e.g. antibodies) which inactivate the virus vector.

Relatively short duration of the period during which the virus vector contacts the desired soft tissue, either due to the immune response described above or due to rapid interaction of all available virus vector particles with the desired tissue.

A desirable virus vector will permit administration that is not significantly inhibited by these phenomena.

Hydrogels are synthetic polymer or biopolymer matrices that are highly hydrated (e.g. at least 50%, by weight, of the hydrogel comprises water). Despite the high degree of hydration of hydrogels, an important characteristic of hydrogels is that they are structurally stable. Commonly used hydrogels include those composed of synthetic components, such as polyacrylamides or poloxamers. Other hydrogels which have been used are composed of a naturally occurring polymer, such as collagen. For example, freeze-dried collagen matrices have been used to deliver plasmid DNA to bone tissue in order to encourage bone regeneration (Fang et al., 1996, Proc. Natl. Acad. Sci. USA 93:5753–5758). However, hydrated collagen gels lack structural integrity. Alginate, a polysaccharide derived from algae, forms an insoluble aggregate in the presence of calcium, and such calcium alginates are known to be effective immobilizing agent. Alginates have been used in combination with polyamines to deliver rotavirus vaccines to gastrointestinal tissues (Moser et al., 1996, Vaccine 14:1235–1238).

Other investigators have incorporated biomaterials, such as enzymes and living cells, into hydrogel matrices (e.g. U.S. Pat. No. 4,004,979, U.S. Pat. No. 4,452,892, U.S. Pat. No. 4,647,536, and U.S. Pat. No. 5,648,252). In some instances, these investigators have demonstrated that the hydrogel-incorporated cells survived or that the hydrogel-incorporated enzymes retained their enzymatic activity. One group of investigators (U.S. Pat. No. 5,529,777) incorporated virus particles into hydrogel and demonstrated the usefulness of hydrogel-incorporated virus particles as a vaccine. However, these investigators do not describe a composition or method for maintaining the infectivity of the virus particles. Of course, such infectivity would be contrary to use of the composition as a vaccine.

The biocompatibility of many hydrogel compositions, combined with their structural strength and biodegradability, recommends the use of hydrogels as virus vector delivery vehicles. Unfortunately, however, many of the synthetic components commonly used to form hydrogels are incompatible with maintaining virus infectivity.

A critical need remains for hydrogel compositions in which virus vectors can be maintained in an infective state, particularly in a localized manner. The hydrogel compositions described herein satisfy this need.

BRIEF SUMMARY OF THE INVENTION

The invention relates to a composition for delivery of a virus vector to an animal cell. The composition comprises a hydrogel precursor mixture having the virus vector suspended therein. The hydrogel precursor mixture is formulated such that it stiffens at physiological temperature and at a physiological calcium level to form a hydrogel matrix containing the virus vector therein in a transfectious form. In one embodiment of the composition described herein, the hydrogel matrix is biodegradable, such as with a collagen hydrogel precursor mixture. When collagen is used, it is preferably type I collagen, such as bovine type I collagen. The biodegradable hydrogel matrix can be made using a precursor mixture which further comprises another component selected from the group consisting of a poloxamer and an alginate. Furthermore, the virus vector can be linked with another component of the hydrogel precursor mixture, such that when the hydrogel matrix is formed, the virus vector is linked with the hydrogel matrix.

Substantially any virus vector can be used in the hydrogel matrix described herein, such as one selected from the group consisting of an adenovirus vector, a lentivirus vector, a retrovirus vector, an adeno-associated virus vector, and a herpesvirus vector. Preferably, the virus vector is an adenovirus vector.

In one embodiment, the hydrogel precursor mixture further comprises an additional component selected from the group consisting of a polycation, a second virus vector, the protein of a protein-ligand pair, and the ligand of a protein-ligand pair. The polycation can, for example, be selected from the group consisting of polylysine, polyarginine, polyornithine, polyhistidine, myelin basic protein, a low molecular weight glycopeptide, a cationic amphiphilic alpha-helical oligopeptide having a repeating sequence, a histone, a galactosylated histone, polybrene, spermine, spermidine, prolamine, polyethylenimine, putrescine, cadaverine, and hexamine. Preferably, the polycation is poly-L-lysine. The protein-ligand pair can, for example, be selected from the group consisting of biotin and an avidin, biotin and streptavidin, an antibody and an epitope to which the antibody specifically binds, and a viral coat protein and a cell-surface molecule with which the viral coat protein specifically binds.

In one embodiment of the composition described herein, the virus vector comprises a transfection indicator, such as one selected from the group consisting of a nucleic acid, a nucleic acid analog, a transcription construct, an antisense oligonucleotide, a ribozyme, and an expression construct.

In yet another embodiment, a component of the hydrogel precursor mixture is bound with an antibody which binds specifically with the virus vector.

In another embodiment of the composition described herein, the virus vector comprises a nucleic acid selected from the group consisting of an expression construct encoding a wound healing therapeutic protein, an expression construct encoding an anti-restenotic protein, an expression construct encoding an anti-oncogenic protein, an anti-restenotic antisense oligonucleotide, and an anti-oncogenic antisense oligonucleotide. The wound healing therapeutic protein can, for example, be selected from the group consisting of TGF-β, FGF, PDGF, PDGF-BB, IGF, M-CGF, BMP, GH, and PTH. The anti-restenotic protein can, for example, be selected from the group consisting of TPA, TGF-β, FGF, Rb, p21, and TK The anti-oncogenic protein can, for example, be encoded by a gene selected from the group consisting of abl, akt2, apc, bcl2α, bcl2β, bcl3, bcr, brca1, brca2, cbl, ccnd1, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf, wnt1, wnt2, wt1, and yes1. The anti-restenotic antisense oligonucleotide can, for example, be selected from the group consisting of a c-myb antisense oligonucleotide, a c-myc antisense oligonucleotide, and a PCNA antisense oligonucleotide. The anti-oncogenic antisense oligonucleotide can, for example, be selected from the group consisting of an abl antisense oligonucleotide, an akt2 antisense oligonucleotide, an apc antisense oligonucleotide, a bcl2α antisense oligonucleotide, a bcl2β antisense oligonucleotide, a bcl3 antisense oligonucleotide, a bcr antisense oligonucleotide, a brca1 antisense oligonucleotide, a brca2 antisense oligonucleotide, a cbl antisense oligonucleotide, a ccnd1 antisense oligonucleotide, a cdk4 antisense oligonucleotide, a crk-II antisense oligonucleotide, a csf1r/fms antisense oligonucleotide, a dbl antisense oligonucleotide, a dcc antisense oligonucleotide, a dpc4/smad4 antisense oligonucleotide, an e-cad antisense oligonucleotide, an e2f1/rbap antisense oligonucleotide, an egfr/erbb-1 antisense oligonucleotide, an elk1 antisense oligonucleotide, an elk3 antisense oligonucleotide, an eph antisense oligonucleotide, an erg antisense oligonucleotide, an ets1 antisense oligonucleotide, an ets2 antisense oligonucleotide, an fer antisense oligonucleotide, an fgr/src2 antisense oligonucleotide, an fli1/ergb2 antisense oligonucleotide, an fos antisense oligonucleotide, an fps/fes antisense oligonucleotide, an fra1 antisense oligonucleotide, an fra2 antisense oligonucleotide, an fyn antisense oligonucleotide, an hck antisense oligonucleotide, an hek antisense oligonucleotide, an her2/erbb-2/neu antisense oligonucleotide, an her3/erbb-3 antisense oligonucleotide, an her4/erbb-4 antisense oligonucleotide, an hras1 antisense oligonucleotide, an hst2 antisense oligonucleotide, an hstf1 antisense oligonucleotide, an ink4a antisense oligonucleotide, an ink4b antisense oligonucleotide, an int2/fgf3 antisense oligonucleotide, a jun antisense oligonucleotide, a junb antisense oligonucleotide, a jund antisense oligonucleotide, a kip2 antisense oligonucleotide, a kit antisense oligonucleotide, a kras2a antisense oligonucleotide, a kras2b. antisense oligonucleotide, an lck antisense oligonucleotide, an lyn antisense oligonucleotide, an mas antisense oligonucleotide, an max antisense oligonucleotide, an mcc antisense oligonucleotide, an met antisense oligonucleotide, an mlh1 antisense oligonucleotide, an mos antisense oligonucleotide, an msh2 antisense oligonucleotide, an msh3 antisense oligonucleotide, an msh6 antisense oligonucleotide, an myb antisense oligonucleotide, an myba antisense oligonucleotide, an mybb antisense oligonucleotide, an myc antisense oligonucleotide, an mycl1 antisense oligonucleotide, an mycn antisense oligonucleotide, an nf1 antisense oligonucleotide, an nf2 antisense oligonucleotide, an nras antisense oligonucleotide, a p53 antisense oligonucleotide, a pdgfb antisense oligonucleotide, a pim1 antisense oligonucleotide, a pms1 antisense oligonucleotide, a pms2 antisense oligonucleotide, a ptc antisense oligonucleotide, a pten antisense oligonucleotide, an raf1 antisense oligonucleotide, a rb1 antisense oligonucleotide, an rel antisense oligonucleotide, an ret antisense oligonucleotide, an ros1 antisense oligonucleotide, an ski antisense oligonucleotide, an src1 antisense oligonucleotide, a tal1 antisense oligonucleotide, a tgfbr2 antisense oligonucleotide, a thra1 antisense oligonucleotide, a thrb antisense oligonucleotide, a tiam1 antisense oligonucleotide, a trk antisense oligonucleotide, a vav antisense oligonucleotide, a vhl antisense oligonucleotide, a waf1 antisense oligonucleotide, a wnt1 antisense oligonucleotide, a wnt2 antisense oligonucleotide, a wt1 antisense oligonucleotide, and a yes1 antisense oligonucleotide.

The invention also relates to an implantable device having a surface coated with a hydrogel matrix containing a virus vector therein in a transfectious form. The hydrogel matrix can, for example, comprise a collagen alginate hydrogel comprising $Ca^{2+}$ ions or a poloxamer-containing collagen hydrogel. The device can, for example, be selected from the group consisting of a wound dressing, a suture, a particle, a vascular stent, an endotracheal tube, and a bulk material. When the device is a vascular stent, the virus vector preferably comprises a nucleic acid selected from the group consisting of an expression construct encoding an anti-restenotic protein and an anti-restenotic antisense oligonucleotide. When the device is a suture, the virus vector preferably comprises a nucleic acid comprising an expression construct which encodes a wound healing protein. When the device is a particle, the virus vector preferably comprises a nucleic acid selected from the group consisting of an expression construct encoding a wound healing therapeutic protein, an expression construct encoding an anti-restenotic protein, an expression construct encoding an anti-oncogenic protein, an anti-restenotic antisense oligonucleotide, and an anti-oncogenic antisense oligonucleotide. The particles preferably have a diameter no greater than about 900 micrometers, and more preferably not greater than about 1 micrometer. When the device is a bulk material, the virus vector preferably comprises a nucleic acid selected from the group consisting of an expression construct encoding a wound healing therapeutic protein, an expression construct encoding an anti-restenotic protein, an expression construct encoding an anti-oncogenic protein, an anti-restenotic antisense oligonucleotide, and an anti-oncogenic antisense oligonucleotide.

The invention further relates to a composition for staged delivery of a first virus vector and a second virus vector to an animal cell. This composition comprises a first hydrogel matrix layer comprising the first virus vector contained therein in a transfectious form and a second hydrogel matrix layer comprising the second virus vector contained therein in a transfectious form. The first hydrogel layer surrounds the second hydrogel layer.

The invention also relates to a method of making a composition for delivery of a virus vector to an animal tissue. This method comprises administering to a body location in fluid communication with the tissue a hydrogel precursor mixture having the virus vector suspended therein.

The hydrogel precursor mixture stiffens upon administration to the body location to form a hydrogel matrix containing the virus vector therein in a transfectious form.

The invention further relates to a method of making a composition for delivery of a virus vector to an animal cell. This method comprises contacting the cell with a hydrogel precursor composition which comprises a collagen, a component selected from the group consisting of a poloxamer and an alginate, and the virus vector at physiological temperature and at a physiological concentration of a polyvalent cation. The hydrogel precursor mixture stiffens to form a hydrogel matrix containing the virus vector therein in a transfectious form. Preferably the hydrogel precursor mixture stiffens at a temperature of about 37° C., the polyvalent cation is $Ca^{2+}$, and concentration of the cation is about 2.5 millimolar.

The invention still further relates to a method of delivering a virus vector to an animal tissue. This method comprises administering to a body location in fluid communication with the animal tissue a hydrogel precursor mixture having the virus vector suspended therein. The hydrogel precursor mixture stiffens upon administration to the body location to form a hydrogel matrix containing the virus vector therein in a transfectious form. Preferably, the hydrogel matrix is administered in contact with the animal tissue. The tissue can, for example, be selected from the group consisting of a wounded tissue, an ischemic tissue, a gastrointestinal tissue, an embryonic tissue, and a fetal tissue. Preferably, the animal is a human.

The invention also relates to a method of delivering a virus vector to an animal cell. This method comprises placing in fluid communication with the cell a composition comprising a hydrogel matrix having the virus vector contained therein in a transfectious form. In one embodiment, the animal cell is outside of the body of the animal from which it was obtained; in another, it is in an animal. In one embodiment of this method, the composition is placed in fluid communication with the cell by placing in fluid communication with the cell an implantable device having a surface coated with the composition. The device can, for example, be selected from the group consisting of a wound dressing, a suture, a particle, a vascular stent, and a bulk material. The cell can, for example, be selected from the group consisting of a cell of a wounded tissue, a cell of an ischemic tissue, a cell of a gastrointestinal tissue, a cell of an embryonic tissue, and a cell of a fetal tissue. The cell can be a cultured animal cell. Preferably, the animal is a human.

The invention further relates to a kit comprising a collagen, a component selected from the group consisting of a poloxamer and an alginate, and an instructional material which describes a method of making a collagen hydrogel matrix which comprises the component and which contains a virus vector therein in a transfectious form. The kit can further comprise a virus vector precursor, such as an adenovirus vector comprising a nucleic acid having a multiple restriction site.

The invention also relates to a composition for storage of a virus vector in a transfectious form. This composition comprises polyvalent metal ions, a hydrogel precursor mixture having the virus vector suspended therein. The hydrogel precursor mixture stiffens at normal storage temperature to form a hydrogel matrix containing the virus vector therein in a transfectious form. In one embodiment, the polyvalent metal ions are calcium ions and are present at a concentration of at least about 0.1 millimolar.

BRIEF DESCRIPTION OF THE DRAWINGS

FIG. 2, comprising

FIG. 3, comprising FIG. 3A depicts a tissue section obtained from an schemic wounded rabbit ear tissue to which the vector had been delivered using a hydrogel composition described herein. FIG. 3B depicts a tissue section obtained from an ischemic wounded rabbit ear tissue to which the vector had been delivered by injection of a suspension of the vector. The magnification in each of FIGS. 3A and 3B is 5×. FIG. 3C depicts a tissue section obtained from an ischemic wounded rabbit ear tissue to which the vector had been delivered using a hydrogel composition described herein at 10× magnification.

DETAILED DESCRIPTION

Figure 1:
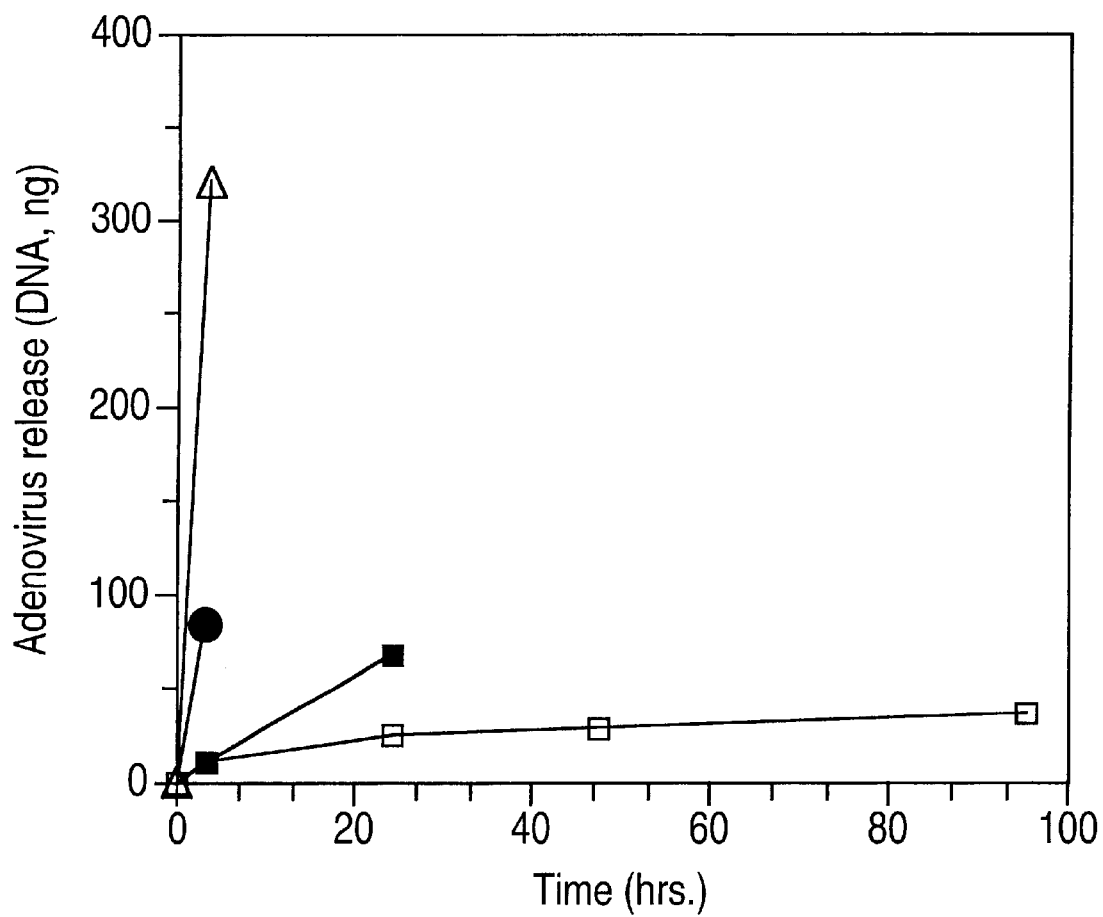
FIG. 1 is a graph which depicts release of adenovirus vector from collagen alginate hydrogel compositions, as assessed using a thiazole orange fluorescent DNA assay, as described herein. Release of virus vector from a hydrogel in a solution comprising 2 milligrams per milliliter of clostridial collagenase is represented by open triangles. Release of virus vector from a hydrogel in a solution comprising 0.2 milligrams per milliliter of clostridial collagenase is represented by filled circles. Release of virus vector from a hydrogel in a solution comprising 0.02 milligrams per milliliter of clostridial collagenase is represented by filled squares. Release of virus vector from a hydrogel in a solution not comprising collagenase is represented by open squares.

The invention is based on the discovery that sustained-release delivery of a virus vector can be improved by providing a composition comprising a hydrogel matrix containing the virus vector therein in a transfectious form. The compositions and methods described herein are particularly useful for delivery of a nucleic acid to a cell or tissue of an animal.

Compared to prior art virus vectors, the compositions described herein, which comprise a virus vector, exhibit reduced immunogenicity and enhanced delivery of the virus vector to desired cells. Furthermore, the compositions described herein minimize inflammation associated with delivery of a virus vector to an animal tissue, presumably by limiting the amount of virus vector to which the tissue is subjected at any point in time. Without wishing to be bound by any particular theory of operation, it is believed that the compositions described herein minimize immunogenicity elicited by the virus vector by sequestering the vector within the hydrogel matrix of the composition, thereby limiting contact between the vector and components of the host immune system. Further without wishing to be bound by any particular theory of operation, it is believed that the composition described herein enhances gene delivery to a target tissue by providing sustained release of the virus vector geometrically close to, and in fluid communication with, the target tissue.

Among other uses, the sustained virus vector release properties of the composition described herein permit long-term fetal exposure to the virus vector of the composition during the period during which fetal immune competence is developed. Thus, the composition described herein can be used to effect in utero immune tolerization of an animal such as a human to a virus vector such as an adenovirus vector. By making an animal having an immune system which tolerates the virus vector of the composition, one is enabled to perform gene therapy upon the animal using the virus vector, in utero, in a neonatal animal, in a juvenile animal, or in an adult animal.

The hydrogel matrix of the compositions can be used to coat or to partially or completely fill cavities in an animal in utero, such as a human fetus, which could not be coated or partially or completely filled without causing serious discomfort or injury to the animal if the animal were an adult. By way of example, the hydrogel precursor mixture described herein can be used to coat or to fill the bronchial passages of a human fetus. Upon delivery to the bronchial passages of the fetus, the mixture stiffens to form a hydrogel matrix. Virus vector released from the hydrogel matrix can deliver, for example, an expressible nucleic acid encoding a wild type CFTR gene to the cells lining the passages or a nucleic acid which encodes such a gene and which is capable of being replicated in those cells. Thus, according to this example, cystic fibrosis can be alleviated or cured in a human fetus in utero.

In one embodiment, the composition described herein comprises a hydrogel precursor mixture having a virus vector suspended therein. When the mixture is exposed to the physiological temperature of an animal such as a human and to the physiological calcium level of an animal such as a human (e.g. ca. 2–3 millimolar), the mixture stiffens to form a hydrogel matrix which is less easily deformed than the hydrogel precursor mixture. Upon formation of the hydrogel matrix, the virus vector is contained within the hydrogel matrix in a transfectious form, and cannot freely diffuse from an interior portion of the hydrogel matrix to a liquid in which the hydrogel matrix is suspended (or a liquid with which the matrix is in contact), with the possible exception of a relatively small quantity of the virus vector which remains loosely and non-covalently associated with the exterior surface of the matrix. If desired, such virus vectors can be rinsed from the surface of the hydrogel using, for example, phosphate buffered saline or another solution comprising ionic species.

In another embodiment, the composition comprises a hydrogel matrix containing a virus vector suspended or attached therein in a transfectious form. The virus vector cannot freely diffuse from an interior portion of the hydrogel matrix to a liquid in which the hydrogel matrix is suspended (or a liquid with which the matrix is in contact), with the possible exception of a relatively small quantity of the virus vector which remains loosely and non-covalently associated with the exterior surface of the matrix. The hydrogel matrix can be part of a multi-layer structure, wherein the structure comprises one or more hydrogel matrix layers, one or more non-hydrogel matrix layers, or both. By way of example, such structures include a multi-hydrogel matrix layer structure, a device having one or more surfaces coated with one or more hydrogel matrix layers, and a hydrogel matrix having one or more surfaces coated with a non-hydrogel material.

Multi-hydrogel matrix layer structures include particles which comprise a first hydrogel matrix layer, comprising a first virus vector contained therein in a transfectious form, and a second hydrogel matrix layer which coats all or a portion of the first hydrogel matrix layer and which comprises a second virus vector contained therein in a transfectious form. The first and second virus vectors can be the same or different. When the particle comprises a first hydrogel matrix layer comprising a first virus vector completely surrounded by a second hydrogel layer comprising a second virus vector, the particle can be used to achieve staged delivery of the first and second virus vectors. According to such staged delivery methods, the second virus vector is delivered to a cell or tissue with which the particle is in fluid communication during a first period during which the first virus vector is not delivered to the cell or tissue, and the first virus vector is delivered to the cell or tissue during a later period, after which all or part of the second hydrogel matrix layer has biodegraded.

In another important embodiments of the invention, the hydrogel matrix coats a surface, such as a surface of an implantable device. Such surfaces and devices comprise the hydrogel matrix at at least one surface, and the virus vector is contained within (e.g. suspended in or attached to) the hydrogel matrix in a transfectious form. Upon implantation of the device, the virus vector is released from the hydrogel matrix in the vicinity of the device, either by biodegradation of the matrix or physical decomposition of the matrix effected, for example, by physical wearing of the surface coated with the matrix or by enzyme-catalyzed hydrolysis of the matrix. The device can be one made solely for the purpose of delivering the virus vector (e.g. particles or bulk materials comprising the hydrogel matrix), or it can be a device having a separate physiological function (e.g. wound dressings or vascular stents comprising the hydrogel matrix).

In another important embodiment of the composition described herein, the hydrogel matrix or the hydrogel precursor mixture is coated with a material which prevents or reduces contact between the matrix or mixture and a fluid which contacts the exterior surface of the material. The purpose of using such a coating can, for example, be to delay contact between the fluid and the matrix or mixture, to contain the matrix or mixture in a cell-permeable, but non-biodegradable, device which can be retrieved after cells have infiltrated the device, to further extend the period over which the virus vector is released from the matrix or mixture, and the like. In a preferred embodiment, the material is a biodegradable polymer such as a biodegradable polylactic-polyglycolic acid (PLGA) copolymer. In another embodiment, the material is a slowly biodegradable material, such as a polycaprolactone or a polyanhydride, or a non-biodegradable polymer, such as a high density polyethylene mesh containing a hydrogel matrix which contains a virus vector therein in a transfectious form. Should it become necessary or desirable to remove the hydrogel from the site at which it has been placed, the non-biodegradable mesh permits simplified removal of the hydrogel by preventing or minimizing both adherence of the hydrogel to the site and dispersion of the hydrogel from the site.

The compositions described herein are particularly amenable to use on implantable devices. The devices can be fashioned from or coated with a hydrogel matrix described herein. In various embodiments:

The hydrogel matrix is used to form or to coat a wound dressing (e.g. a bandage or a hernia repair mesh), and the virus vector comprises an expression construct encoding a wound healing therapeutic protein.

The hydrogel matrix is used to form or to coat a vascular stent, and the virus vector comprises either an expression construct encoding an anti-restenotic protein or an anti-restenotic oligonucleotide.

The hydrogel matrix is used to form or, preferably, to coat a suture, and the virus vector comprises an expression construct encoding a wound healing therapeutic protein.

The hydrogel matrix is used to form or to coat a particle or a bulk material, and the virus vector comprises either an expression construct encoding an antioncogenic protein or an anti-oncogenic antisense oligonucleotide.

The hydrogel matrix is used to form, to fill, or to coat a tissue scaffold, particularly a soft tissue scaffold, comprises a cell attractant, the virus vector comprises a nucleic acid which promotes growth of cells into the scaffold and survival of cells in the scaffold.

The hydrogel matrix is used to form, to fill, or to coat a peri-intestinal implant at the site of a small or large bowel anastomosis, or is otherwise placed in fluid communication with this site, and the virus vector comprises an expression construct encoding a wound healing therapeutic protein; expression of the protein at the site promotes healing of the anastomosis and lessens the risk of colostomy.

The hydrogel matrix is used to form, to fill, or to coat a perivascular graft implant at the site of a venous or arteriovenous anastomosis, and the virus vector comprises an expression construct encoding a wound healing therapeutic protein; expression of the protein at the site expression of the protein at the site promotes healing of the anastomosis and lessens the risk of graft obstruction.

The hydrogel matrix is used to form or to coat an arterio-venous shunt used in dialysis procedures, to form or to coat a stent positioned within such a shunt, or is otherwise placed in fluid communication with the site of such a shunt, either during or after implantation of the shunt, and the virus vector comprises an expression construct encoding a wound healing therapeutic protein; expression of the protein at the site promotes healing of tissue at the site of the shunt and improves or maintains patency of the shunt.

The hydrogel matrix is used to form or to coat an endotracheal device (e.g. an endotracheal tube or endotracheal stent), and the virus vector comprises an expression construct encoding a wound healing therapeutic protein; expression of the protein alleviates, inhibits, or prevents intratracheal granulation or formation of intratracheal strictures.

These embodiments are, of course, merely non-limiting examples of how the compositions described herein can be used to deliver a virus vector to cells or tissues in an animal, either in vivo or in vitro.

When the virus vector comprises an expression construct, it is preferred that the expression construct be targeted to the nucleus. Nuclear targeting can, for example, be achieved by attaching a protein to the surface of a virus using a conjugated virus-specific antibody. This method has been demonstrated using an antibody linked to basic fibroblast growth factor (bFGF), wherein the antibody binds specifically with an adenovirus. Nuclear targeting of bFGF in this manner has been demonstrated by others to enhance expression through both an FGF receptor entry mechanism and enhanced nuclear entry. Nuclear entry of plasmid DNA and viruses can also be enhanced using polymers or specific protein and peptide sequences, as described in the art (Pollard et al., 1998, J. Biol. Chem. 273:7507–7511; Sebestyen et al., 1998, Nature Biotechnol. 16:80–85; Neill et al., 1995, Biochem. Soc. Trans. 23:346S; Peeples et al., 1992, J. Virol. 66:3263–3269).

As described herein, the components of the compositions described herein, including the components of the hydrogel precursor mixture, the virus vector, the compositions and conditions used to stiffen the hydrogel precursor mixture to form the hydrogel matrix, and any additional components of the virus vector or the hydrogel precursor mixture or the hydrogel matrix can be varied quite liberally. It is preferred to optimize the composition prior to its use in vivo or ex vivo to effect delivery of the virus vector to one or more cells or tissues of an animal. The process of opting the compositions can be performed using an in vitro model of the cells to which the virus vector is to be delivered or an in vivo model of the cells in an animal of a species different than the species to which the virus vector is ultimately to be delivered. It is important that the virus vector be capable of transfecting both cells in the model system and the cells in the animal to which the virus vector is ultimately to be delivered. Methods of selecting cells which are susceptible to transfection with a virus vector, as well as methods of testing whether cells are susceptible to transfection with a virus vector are known in the art, and can be used to select appropriate model cells. Preferably, the model cells are of the same type and the same species as the cells to which the virus vector is ultimately to be delivered. In vitro or in vivo experiments to test various components of the composition, methods of preparing such compositions, and the like, can be performed using the appropriately selected model cells in order to identify an optimal composition prior to administration of that composition to the desired animal. By way of example, model cells which are useful for optimizing compositions for delivery of a virus vector to various human tissues include primary human fibroblast in in vitro culture, 293 kidney epithelial cells in in vitro culture, and A10 vascular smooth muscle cells in in vitro culture.

Hydrogel matrices, and hydrogel precursor mixtures used to form them, can be tested to determine whether a virus vector contained or suspended therein remains in a transfectious form using substantially any method known for testing the transfectiousness of a virus vector, including, for example, plaque assays, assays which detect the presence of a nucleic acid of the vector in target cells, and assays which detect the activity in target cells of an enzyme encoded by a nucleic acid of the vector. When a hydrogel matrix is tested, it is preferable to degrade the matrix, either by providing an enzyme having matrix-degrading activity or by physically degrading the matrix, such as by crushing or grinding. The same methods can be used to determine whether addition or removal of a hydrogel matrix component or a hydrogel precursor mixture component affects the transfectiousness of a virus vector.

The virus vector of the compositions described herein is preferably present only in the interior portion of the hydrogel matrix. However, the virus vector can optionally be present at the exterior surface of the matrix as well. In one embodiment, a multi-layer hydrogel matrix is prepared in discrete layers, a virus vector being contained within each layer of the matrix in a transfectious form. The virus vectors in the layers can be the same or different, and the compositions of the hydrogel matrices in the layers can also be the same or different.

Exemplary materials which can be used in the compositions of the invention are now described. It is understood, however, that the materials described herein represent only non-limiting examples of materials which can be used. In light of the present disclosure, it will be evident to the skilled artisan how materials which are not specifically listed here, or which are hereafter developed or discovered, can be used to generate the composition of the invention.

The Virus Vector of the Composition

The virus vector can be substantially any virus vector. By way of example, the virus vector can be an adenovirus vector, a lentivirus vector, a retrovirus vector, an adeno-associated virus vector, or a herpesvirus vector. In a preferred embodiment, the virus vector which is used in the compositions and methods described herein is an adenovirus vector. Adenovirus vectors are the most potent agents investigated thus far for gene therapy. However, their clinical use has been limited because of immunogenicity and toxicity concerns. In particular, a type 5 replication defective adenovirus vector comprising an expression construct which comprises a cytomegalovirus (CMV) promoter is preferred. The expression construct preferably encodes a therapeutic protein, such as human platelet derived growth factor BB (PDGF-BB) or a protein, the presence of which can be conveniently assayed, such as a beta-galactosidase protein.

The nucleic acid carried by the virus vector in the present invention can be, by way of example and not limitation, an oligonucleotide or polynucleotide such as an antisense DNA molecule, an antisense RNA molecule, a catalytic RNA molecule or a catalytic RNA/protein complex (i.e. a "ribozyme"), an expression construct comprising a DNA molecule encoding a protein such as a therapeutic protein, a transcribable construct comprising a DNA molecule encoding a ribozyme, a viral genome fragment such as a viral DNA or RNA molecule, an RNA molecule encoding a protein such as a therapeutic protein, a plasmid, a cosmid, a DNA molecule encoding a portion of the genome of an organism, a cDNA molecule, a gene fragment; or a DNA molecule in any of its superstructural forms, including single-stranded DNA, double stranded DNA, supercoiled DNA, triple-helical DNA, Z-DNA, and the like.

The nucleic acid of the virus vector described herein can be prepared or isolated by any conventional means typically used to prepare or isolate nucleic acids. For example, DNA and RNA molecules can be chemically synthesized using commercially available reagents and synthesizers by methods that are known in the art (e.g., Gait, 1985, In: *Oligonucleotide Synthesis: A Practical Approach*, IRL Press, Oxford, England). RNA molecules can also be produced in high yield via in vitro transcription methods using plasmids such as SP65 (available from Promega Corporation, Madison, Wis.). The nucleic acids can be purified by any suitable means, as many such means are known in the art. For example, the nucleic acids can be purified by reverse-phase or ion exchange HPLC, size exclusion chromatography, or gel electrophoresis. Of course, the skilled artisan will recognize that the method of purification will depend in part on the size of the DNA to be purified. Nucleic acids suitable for delivery using a virus vector can also be prepared using any of the innumerable recombinant methods which are known or are hereafter developed.

Nucleic acids having modified internucleoside linkages can also be used in the virus vector described herein. Nucleic acids containing modified internucleoside linkages can be synthesized using reagents and methods that are known in the art. For example, methods for synthesizing nucleic acids containing phosphonate, phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2-$), dimethylene-sulfoxide ($-CH_2-SO-CH_2-$), dimethylene-sulfone ($-CH_2-SO_2-CH_2-$), 2'-O-alkyl, and 2'-deoxy-2'-fluorophosphorothioate internucleoside linkages are known in the art (e.g. Uhlmann et al., 1990, Chem. Rev. 90:543–584; Schneider et al., 1990, Tetrahedron Lett. 31:335).

The nucleic acid can, for example, be a therapeutic agent, such as an antisense DNA molecule that inhibits mRNA translation. Alternatively, by way of example, the nucleic acid can encode a therapeutic agent, such as a transcription or translation products which, when expressed by a cell to which the nucleic acidcontaining composition is delivered, has a favorable therapeutic effect upon the cell. Exemplary therapeutic transcription products include antisense RNA molecules, ribozymes, viral genome fragments, and the like. Exemplary therapeutic translation products include therapeutic proteins, such as a membrane proteins, transcription factors, intracellular proteins, cytokine binding proteins, wound healing proteins, anti-restenotic proteins, anti-oncogenic proteins and the like.

In a preferred embodiment of the invention, the nucleic acid of the virus vector is a DNA molecule that encodes gene products that stimulate or promote healing of wounded or damaged tissues in vivo or alleviate the symptoms of disease. Particularly preferred are therapeutic proteins, such as growth factors and hormones. Particularly preferred growth factors are transforming growth factor-beta (TGF-β; Cox, D.A., 1995, *Cell Biology International* 19: 357 –371), acidic fibroblast growth factor (FGF; Slavin, 1995, Cell Biol. Intl. 19:431–444), platelet derived growth factor (PDGF), PDGF-BB, insulin like growth factor (IGF), macrophage-colony stimulating factor (M-CSF), and bone morphogenic protein (BMP); particularly preferred hormones are human growth hormone (GH) and human parathyroid hormone (PTH).

In another preferred embodiment of the invention, the nucleic acid of the virus vector is selected from an expression construct encoding an anti-restenotic protein and an anti-restenotic antisense oligonucleotide. Exemplary anti-restenotic proteins include tissue plasminogen activator (TPA), TGF-β, FGF, Tetinoblastoma protein (Rb), p21, and thymidine kinase (TK). Exemplary anti-restenotic antisense oligonucleotides include a c-myb antisense oligonucleotide, a c-myc antisense oligonucleotide, and a PCNA antisense oligonucleotide.

In another preferred embodiment of the invention, the nucleic acid of the virus vector is selected from an expression construct encoding an anti-oncogenic protein and an anti-oncogenic antisense oligonucleotide. Exemplary anti-oncogenic proteins include those encoded by the following genes: abl, akt2, apc, bcl2α, bcl2β, bcl3, bcr, brca1, brca2, cbl, ccndl, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lcy, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf1, wnt1, wnt2, wt1, and yes1. Exemplary anti-oncogenic antisense oligonucleotides include those which inhibit transcription or translation of one of the genes listed in the preceding sentence, and are designated "anti-xxx antisense oligonucleotides," wherein xxx is the gene, the transcription or translation of which is inhibited by the oligonucleotide.

Modified gene sequences, i.e. genes having sequences that differ from the gene sequences encoding the native proteins, are also encompassed by the invention, so long as the modified gene still encodes a protein that exhibits the biological activity of the native protein, at a greater or lesser level of activity. These modified gene sequences include modifications caused by point mutations, modifications due to the degeneracy of the genetic code or naturally occurring allelic variants, and further modifications that are introduced by genetic engineering, i.e., by the hand of man, to produce recombinant nucleic acid molecules.

The nucleic acid of the virus vector described herein can be recombinantly engineered into a variety of known host vector systems that provide for replication of the nucleic acid on a large scale for the preparation of a composition described herein. These vectors can be designed, using known methods, to contain the elements necessary for directing transcription, translation, or both, of the nucleic acid. Methods which are known to the skilled artisan can be used to construct expression constructs having the protein coding sequence operably linked with appropriate transcriptional/translational control signals. These methods include in vitro recombinant DNA techniques and synthetic techniques (see, e.g. Sambrook et al., 1989, *Molecular Cloning: A Laboratory Manual*, Cold Spring Harbor Laboratory, New York; Ausubel et al., 1997, *Current Protocols in Molecular Biology*, John Wiley & Sons, New York).

The nucleic acid encoding the protein(s) of interest can be operatively associated with a variety of different promoter/regulator sequences. The promoter/regulator sequences can be selected to optimize expression of therapeutic amounts of protein. In some instances, the promoter/regulator sequences can be constitutive or inducible promoters and can be used under the appropriate conditions to direct high level or regulated expression of the gene of interest. Preferably, the nucleic acid encoding the protein(s) of interest is operably liked with a CMV promoter, although other promoters can be used.

It is also within the scope of the invention that the nucleic acid of the virus vector described herein contains a plurality of protein-coding regions, combined on a single genetic construct under control of one or more promoters, or prepared as separate constructs of the same or different types. Alternatively, the two or more protein-coding regions can be under the transcriptional control of a single promoter, and the transcript of the nucleic acid can comprise one or more internal ribosome entry sites interposed between the protein-coding regions. Thus, an almost endless combination of different genes and genetic constructs can be employed. Any and all such combinations-are within the scope of the present invention.

The virus vector of the composition described herein can be used to deliver molecules other than nucleic acids to targeted cells. Examples of such other molecules include proteins, polyamines, and known pharmaceutical compositions. These molecules can be incorporated into the virus vector by generating the virus vectors in cells which comprise such molecules.

The Hydrogel Precursor Mixture

The hydrogel precursor mixture described herein can be substantially any composition which, when a virus vector is suspended therein and the mixture is thereafter subjected to the physiological temperature of an animal such as a human and the physiological concentration of a multivalent cation in an animal such as a human, stiffens to form a hydrogel matrix containing the virus vector therein in a transfectious form.

The hydrogel precursor mixture preferably comprises a collagen, more preferably a type I collagen, such as human or bovine type I collagen. It is important that the components of the precursor mixture be chosen to provide for stable chemical assembly of the hydrogel. Furthermore, the components should have a relatively benign chemical nature, such that they preferably do not damage or alter viral vector activity (e.g. cell binding or entry characteristics). If chemical moieties on the surface of or within the interior of the hydrogel are to be modified (e.g. by attachment of an antibody) after formation of the hydrogel, it is likewise important that the reagents chosen for performing such modifications not damage or alter viral vector activity.

In one embodiment, the hydrogel precursor mixture components are selected to yield self-assembling biopolymers. Examples of such self-assembling biopolymers include collagens, laminins, pro-elastin peptides, and the like. The precursors of self-assembling synthetic polymers can be selected such that the polymers will array themselves according to domains. For example, hydrophilic, relatively charge-neutral polyamino acids such as polyglycine can be modified to function in this capacity. Polyamino acids can be linked by using carboxy-activating cross-inkers such as water soluble carbodiimides. Such cross-linkers can be used to connect self-assembling proteins or other self-assembling macromolecules to the polyamino acids. Examples of this approach include carbodiimide linkage of type I collagen or laminin to polylysine. Alternatively, other hydroxylated entities can be linked in the same manner, such as self-assembling polymers (hydrogels) such as the poloxamers. Also, hydroxylated polymers such as polyvinyl alcohol (PVA) can be linked with polyamino acids using an epoxy-activation approach, such as is known in the art. The higher the molecular weight of the PVA used, the more rapid the time course of self-assembly will be.

The hydrogel can, alternatively, be generated using a receptor-containing precursor and a corresponding ligand-containing precursor which self-assemble to form receptor-ligand complexes. Either or both of the receptor-containing precursor and the corresponding ligand-containing precursor can be prepared using recombinant techniques. For example, a hydrogel of this type could be made using a precursor comprising at least a segment of the FGF receptor binding site conjugated with a biopolymer such as purified type I collagen and another precursor comprising FGF protein conjugated to the same or a different biopolymer. Likewise, other such hydrogels could be generated using receptor-ligand pairs wherein the ligand and the receptor are each conjugated to the same or a different type of polymer, and wherein the pairs are, for example, antibody-antigen pairs or avidin-biotin (e.g. streptavidin-biotin).

In another embodiment, the hydrogel precursor mixture comprises a poloxamer. Sustained-release delivery of a virus vector can be improved by providing the vector in the form of a hydrogel precursor mixture comprising the vector and a poloxamer. The mixture can comprise a poloxamer solution having the vector suspended therein, or it can comprise a poloxamer having the vector bound therewith (e.g. by means of a cross-linking agent such as a carbodiimide or by means of a virus binding agent such as an antibody linking the vector and the poloxamer). The poloxamer-containing hydrogel precursor mixture is preferably formulated such that it is liquid at a temperature lower than the physiological temperature of the animal to which it is to be administered, but solidifies to form a solid or semi-solid matrix having the vector therein in a transfectious form at the physiological temperature of the animal. The virus vector can be released from the matrix as it degrades, as physiological ion concentrations of the animal displace vector associated with the matrix, as an enzyme normally found in the animal catalyzes degradation of the matrix, or some combination thereof. Because the poloxamer solution is initially liquid but solidifies upon heating, it can be poured, injected, sprayed, or otherwise administered in a manner in which the solid/semi-solid matrix that is formed by heating fills (entirely or partially), coats, or surrounds one or more cells or tissues in the animal.

The poloxamer-containing hydrogel precursor mixture preferably comprises another polymeric material, such as a collagen. In one embodiment, the mixture comprises type I collagen (e.g. bovine) and a sufficient concentration of a poloxamer that the mixture rapidly gels (e.g. forming a gel which does not substantially flow under the influence of gravity alone within 10, 5, 3, 2, or even 1 second) at the physiological temperature of the portion of the animal body to which the mixture is to be provided.

Solid and semi-solid poloxamer-containing matrices are biodegradable, and release infectious virus vector particles that are contained therein or bound therewith in a sustained fashion. Thus, the poloxamer- and virus vector-containing compositions described herein are useful for providing transfectious virus vector particles to a body location over a prolonged period of time, such as for hours, days, weeks, months, or even years. Furthermore, because the composition described herein can be solidified at a discrete body location, this composition is useful for forming an in vivo depot of transfectious virus vector that provides a sustained (e.g. continuous) supply of vector to a target tissue which the composition contacts or with which the composition is in fluid communication.

Poloxamers are detergents. Poloxamers and other detergents are commonly used in the prior art as agents for sterilizing surfaces and materials, based at least in part on the known ability of detergents to inactivate viruses. Thus, the discovery that poloxamers can be used to enhance the kinetics of transfectious virus vector release from a solid or semi-solid material (i.e. rather than inactivating the virus vector over time and thereby rendering it non-transfectious) was unexpected and counter-intuitive.

A particular class of poloxamers which are contemplated include the poloxamers which are sold under the trade name Pluronics™ (BASF), including a product designated Pluronics™ F-127 (also designated poloxamer 407). Poloxamer 407 is a biocompatible polyoxypropylene-poloxyethylene block copolymer having an average molecular weight of about 12,500 and a polyoxypropylene fraction of about 30%. Exemplary poloxamer solutions which can be used in the compositions and methods described herein include those in which poloxamer 407 is present at a concentration of at least about 1, 2, 5, 10, 15, or 20% (w/v) of the poloxamer, and preferably at a concentration of about 25% (w/v). Mixtures of poloxamer 407 solution and a virus vector are liquid at 4° C., and solidify almost instantaneously upon heating to 37° C. (e.g. substantially upon contact with a surface having a temperature of 37° C.). Mixtures which contain another polymer (e.g. bovine type 1 collagen) are similarly liquid at 4° C. and solidifly rapidly upon heating to 37° C. Thus, such mixtures can be administered to a human body location in liquid form and solidify at that location.

When a poloxamer-containing hydrogel precursor mixture or matrix is used to deliver a virus vector to a cell or tissue, the vector is preferably bound, covalently or non-covalently, with the poloxamer or with another component of the mixture or matrix, as described elsewhere herein.

A hydrogel precursor mixture can further comprise an alginate, such as sodium alginate. Alginate, or a comparable co-constituent, serves to strengthen a hydrogel made using the mixture. When such a hydrogel mixture is administered to a body cavity of an animal, the hydrogel mixture forms a hydrogel, wherein the alginate or comparable co-constituent serves to maintain the gel intact at the site in the desired configuration. Such a strengthened hydrogel continues to contain and mediate controlled release of the virus. Other strengthening co-constituents which can be used include, for example, virtually any cross-linking agent which is chemically compatible with continued viral function, high molecular weight polysaccharides, water insoluble lipids in a liposome-like configuration, complex carbohydrates (e.g. alginate) which have decreased solubility in the presence of certain cations, highly hydrated polymers (e.g. methyl cellulose), and glycosaminoglycans. When the co-constituent is alginate and the hydrogel precursor mixture comprises a type I collagen precursor, the proportion of type I collagen:alginate is preferably from about 7:3 to about 4:6, on a dry weight basis, although higher and lower proportions can also be used. Such mixtures can be made by combining dry (i.e. lyophilized or freeze-dried) collagen and alginate compositions, and thereafter re-suspending the compositions in an aqueous liquid. This mixture can also be made by combining a dry composition of a virus vector either before or after addition of the aqueous liquid to form the hydrogel precursor mixture. Preferably, however, the collagen, the alginate, and the virus vector are combined in the form of suspensions of these ingredients. Of course, combinations of suspensions and dry forms of the ingredients can be used to form the hydrogel precursor mixture described herein. Alternatively, the mixture can further comprise a source of $Ca^{2+}$, or other polyvalent cations, provided the precursor mixture is maintained at a low temperature (i.e. lower than body temperature; e.g. 20° C., 10° C., 4° C., or even lower).

In one embodiment, the hydrogel precursor mixture is prepared in the form of a liquid which flows at the physiological temperature of an animal to which it is to be administered, (e.g. 37° C. if the animal is a human). Preferably, the viscosity of the hydrogel precursor mixture at 37° C. is not preferably greater than about 2 Newton-seconds per square meter, and is more preferably not greater than about 1.5 Newton-seconds per square meter. Of course, mixtures having higher or lower viscosity can also be used. Alternatively, the hydrogel precursor mixture can be prepared such that it flows freely at 37° C., particularly where a body cavity in an animal is to be filled by gravitationally providing the precursor mixture to the cavity remotely (e.g. by positioning an animal such that a lesion within the animal's bladder is at the lowest point of the bladder and then providing the hydrogel precursor mixture to the lumen of the bladder).

In another embodiment, the hydrogel precursor mixture preferably does not flow substantially at the physiological temperature of an animal to which it is to be administered, (e.g. 37° C. if the animal is a human).

For example, when the hydrogel precursor mixture is to be injected into a body location of an animal using a device having a narrow channel (e.g. a needle, cannula, or piece of flexible, narrow bore tubing), the mixture should be in a liquid or easily-deformable form. However, when the hydrogel precursor mixture is to be used to generate solid forms, such as particles, bulk materials, or devices, or to coat particles, bulk materials, or devices, the mixture should have a viscosity sufficiently high that the mixture retains its geometrical form after generation of the matrix but prior to formation of the hydrogel matrix. The viscosity of the mixture can even be sufficiently high that the mixture retains its geometrical form regardless of whether it is suspended in an aqueous liquid. It is understood that the viscosity of the hydrogel precursor mixture can be altered in numerous ways that will be understood by the skilled artisan in view of the present disclosure. By way of example, increasing the water content of the mixture, increasing the temperature, or decreasing the length of the alginate or collagen polymer chains, will decrease the viscosity of the mixture, and the reverse would also be true. The viscosity of the mixture can alternatively be increased by including within the mixture one or more of a high molecular weight biopolymer (e.g. a glycosaminoglycan), a self-assembling biopolymer (e.g. laminin), a synthetic water soluble cross-linking agent (e.g. N-succinimidyl-3-(2-pyridyldithio) propionate {SPDP}), and a water soluble carbodiimide.

The hydrogel precursor mixture can further comprise any number of additional ingredients. Such additional ingredients can include, for example, buffers, drugs and other pharmaceutically active compounds, targeting molecules (e.g. antibodies and cell-specific oligosaccharides), cross-linking agents (e.g. dithiothreitol and glutaraldehyde), other virus vectors, other nucleic acid vectors (e.g. naked DNA), polycations (e.g. polylysine), high molecular weight biopolymers (e.g. a glycosaminoglycan), self-assembling biopolymers (e.g. laminin), synthetic water soluble cross-linking agents (e.g. SPDP), water soluble carbodiimides, and the like. These additional components can be combined with the hydrogel precursor mixture prior to forming the hydrogel matrix, attached to or otherwise associated with the exterior surface of the hydrogel matrix after formation thereof, injected or infused into the interior of the hydrogel matrix, or diffused through or within the hydrogel matrix, if the additional component has a molecular size which permits such diffusion. In various embodiments, the additional component can be covalently or non-covalently bonded with the collagen of the hydrogel precursor mixture or the hydrogel matrix, covalently or non-covalently bonded with the alginate of the hydrogel precursor mixture or the hydrogel matrix, dissolved or suspended in the hydrogel precursor mixture or the hydrogel matrix, contained within or coated with hydrogel precursor mixture or the hydrogel matrix, dissolved or suspended within an aqueous liquid in which the hydrogel precursor mixture or the hydrogel matrix is suspended, or the additional component can be used to coat or otherwise contain the hydrogel precursor mixture or the hydrogel matrix described herein.

The Hydrogel Matrix

The hydrogel matrix described herein can be formed from any of the hydrogel precursor compositions described herein. Preferably, the hydrogel matrix comprises type I collagen and an alginate, a collagen-poloxamer mixture, or a poloxamer having a virus vector bound therewith. The hydrogel matrix preferably has a sufficiently high viscosity (i.e. a sufficiently low deformability), that the hydrogel does not deform solely due to the influence of gravity when exposed to aqueous conditions at 37° C. and at a pH of 7.4 or lower. The hydrogel matrix can thus have a rigidity that is from jelly-like to substantially rigid. In one embodiment, the hydrogel mixture resiliently deforms in response to normal internal body forces in an animal (e.g. forces resulting from the impact of one organ upon another due to movement of the animal). It is understood that the deformability of the hydrogel matrix can be controlled by altering the length of the collagen and alginate polymer chains in the matrix, by changing the concentration of the polyvalent cation in the aqueous liquid with which the hydrogel precursor mixture is contacted in order to form the hydrogel matrix, by changing the duration of the period of time during which the hydrogel precursor mixture is contacted with the aqueous liquid containing the polyvalent cation, by lowering the temperature of the hydrogel matrix, and the like.

The concentration of the virus vector in the hydrogel matrix described herein can vary from nearly no virus particles to approximately the concentration of the virus vectors in a dried virus vector suspension (i.e. precipitated virus particles). The concentration of the virus vector in the hydrogel matrix described herein can be controlled, for example, by regulating the concentration of virus vector suspended in or bound with a component of the hydrogel precursor mixture, by withdrawing water from the hydrogel matrix, or by permitting the hydrogel matrix to absorb water after forming the matrix. The hydrogel matrix can even be dried (e.g. lyophilized or freeze-dried) to generate a matrix which can be used to deliver the virus vector contained therein to a cell or tissue either by administering the dried hydrogel matrix to a liquid, preferably an aqueous liquid, in fluid communication with the cell or tissue or by re-hydrating the dried hydrogel matrix and thereafter administering the re-hydrated hydrogel mixture in fluid communication with the cell or tissue.

The virus vector is contained within the hydrogel matrix described herein is in a transfectious form. The transfectiousness of the virus vector can be maintained by careful selection of the components of the hydrogel precursor mixture and the hydrogel matrix. It is important that components not inhibit the ability of the virus vector to recognize the cells desired to be transfected by the vector, the ability of the virus vector to bind with those cells, or the ability of the vector to transfer the nucleic acid carried by the vector into the interior of those cells. The ability of one or more components to inhibit one of these processes can be assessed using the assays described herein, and other known transfection assays. The component can be tested in the presence or absence of the other components of the hydrogel matrix. Examples of potential hydrogel components which are known to inhibit transfectiousness of virus vectors include metallic catalysts, detergents, polycations, and organic solvents. These compounds should therefore be avoided or minimized in the hydrogel matrices and hydrogel precursor mixtures described herein.

Polyvalent Cations

The polyvalent cation used to stiffen a hydrogel precursor mixture, when necessary or desired, can be substantially any polyvalent cation. When the hydrogel precursor mixture comprises an alginate, such as the collagen- and alginate-containing hydrogel precursor mixture described herein, the polyvalent cation is preferably $Ca^{2+}$. Other polyvalent cations which can be used in place of $Ca^{2+}$ include $Mg^{2+}$, $Al^{3+}$, $La^{3+}$, and $Mn^{2+}$. Polyamino acids that are polycationic (e.g. polylysine and polyarginine) can be used in place of polyvalent elemental cations.

The polyvalent cation can be supplied in the form of a solid salt comprising the cation or a solution, preferably an aqueous solution comprising $Ca^{2+}$. A preferred salt is $CaCl_2$, although it is understood that other water soluble calcium salts are also useful.

A polyvalent cation can be used to stiffen the hydrogel precursor mixture in order to form the hydrogel matrix, particularly when the mixture comprises a material (e.g. an alginate) that gels in the presence of such cations. The polyvalent cation can be contacted with the hydrogel precursor mixture after the mixture is formed or at the same time the mixture is formed. For example, a hydrogel precursor mixture can comprise two suspensions, one comprising collagen and polyvalent cation, the other comprising alginate and virus vector.

The concentration of the polyvalent cation which is used, the duration for which the polyvalent cation-containing solution or suspension is contacted with the hydrogel precursor mixture, and the manner in which the polyvalent cation-containing solution or suspension is contacted with the hydrogel precursor mixture can be used to control the stiffness of the hydrogel matrix which is formed thereby. When the hydrogel matrix is formed outside the body of an animal to which the matrix is to be administered, the concentration of the polyvalent cation can be less than, equal to, or greater than the physiological level of the polyvalent cation in the animal, and is preferably approximately equal to the physiological level of the polyvalent cation in the animal. It is recognized that some hydrogel matrices included within the scope of the invention (e.g. poloxamer-containing matrices) are relatively insensitive to ion concentration. Such matrices are nonetheless useful, as described herein, so long as the matrices stiffen at the physiological temperature and ion concentration anticipated in the subject.

By way of example, a hydrogel matrix having an approximately uniform stiffness throughout can be formed by contacting the corresponding hydrogel precursor mixture with a solution comprising a high concentration (e.g. 2.5 millimolar) of $Ca^{2+}$ for a prolonged period, such as for one or two hours or longer. Alternatively, a hydrogel matrix having an approximately uniform stiffness throughout can be formed by generating a hydrogel matrix by combining a first suspension comprising type I collagen and $Ca^{2+}$ ions with a second suspension comprising an alginate and the virus vector to be contained within the hydrogel matrix.

Further by way of example, a hydrogel matrix which is stiffer near the exterior surface thereof than at an interior portion thereof can be made by briefly contacting a hydrogel precursor mixture with a solution comprising a high concentration of $Ca^{2+}$ for a brief period, such as for less than an hour, or even for five minutes or less. It is understood that, over time, $Ca^{2+}$ ions located near the exterior surface of the hydrogel matrix formed thereby can be able to diffuse toward the interior portion of the matrix, thereby decreasing the difference between the stiffness of the matrix near the exterior surface thereof and the stiffness of the matrix at the interior portion thereof.

Still further by way of example, a hydrogel matrix which is stiffer at an interior portion thereof than at the exterior surface thereof can be made by contacting a $Ca^{2+}$-containing particle, material, or device, with a hydrogel precursor mixture of the composition. $Ca^{2+}$ ions released or diffusing from the particle, material, or device, cause the mixture to stiffen at or near the surface(s) at which the mixture contacts the particle, material, or device, thereby forming a hydrogel matrix at the surface(s). In this way, a sustained release composition of a drug can be formed by contacting a calcium salt of the drug with a hydrogel precursor mixture described herein. Similarly, a device having one or more surface coated with the hydrogel matrix described herein can be made by coating the device with a calcium salt (if the device itself does not comprise calcium in a form in which it can be released into solution in the form of $Ca^{2+}$ ions), and thereafter contacting the coated device with a hydrogel precursor mixture described herein (e.g. an alginate-containing mixture).

Non-Hydrogel Materials Associated with the Hydrogel Precursor Mixture or the Hydrogel Matrix A hydrogel matrix or a hydrogel precursor mixture of the invention can, as described herein, be associated with another hydrogel matrix or another hydrogel precursor mixture. Alternatively, however, a hydrogel matrix or a hydrogel precursor mixture can, as described herein, be associated with a non-hydrogel material. For example, the matrix or mixture can be covalently or non-covalently bonded to the non-hydrogel material, the matrix or mixture can be coated with or embedded in the non-hydrogel material, or the non-hydrogel material can be coated with or embedded in the matrix or mixture.

The chemical identity of the non-hydrogel material is not important, as practically any material, including a solid, a liquid, or a gas, can be combined with a hydrogel matrix or a hydrogel precursor mixture described herein. Furthermore, the non-hydrogel material which is used can be non-biodegradable or biodegradable. Exemplary non-hydrogel materials include implantable devices, drugs and other pharmaceutically-active compounds, pharmaceutically acceptable carriers, polycations, gene vectors, ions and salts, imaging agents, wound dressings, tissue scaffolds (particularly soft tissue scaffolds), and the like.

In certain embodiments, the non-hydrogel material is a polymeric material. The polymers can be a naturally-occurring polymer or a synthetic polymer. Discussion and a non-limiting list of suitable polymers can be found in Mathiowitz et al., P.C.T. publication number WO95/24929 (particularly at pages 6–9), and Goldstein et al., P.C.T. publication number WO97/47254 (particularly pages 22–35). Polymers useful in the compositions described herein include biocompatible biodegradable polymers such as polylactic acid, polyglycolic acid, polycaprolactone, and copolymers thereof. In preferred embodiments, the biocompatible biodegradable polymer is a copolymer of polylactic acid and polyglycolic acid (PLGA copolymer). Also preferably, the proportion of lactate monomers to glycolate monomers in the PLGA copolymer ranges from near infinity (i.e. the polymer comprises essentially only lactate monomers) to a lactate:glycolate ratio of about 25:75. It is understood that the higher the proportion of lactate monomers to glycolate monomers is, the less rapidly the copolymer will be biodegraded. Similarly, a copolymer having a relatively low lactate:glycolate monomer ratio (i.e. 50:50 or 25:75) will release the virus vector at a rate greater than the rate of a copolymer having a relatively high lactate:glycolate monomer ratio (i.e. 75:25 or 100:1). Other suitable biocompatible biodegradable polymers include polyesters such as polyglycolides, polyanhydrides, polyacrylates, polyalkyl cyanoacrylates such as n-butyl cyanoacrylate and isopropyl cyanoacrylate, polylactic-coglycolides (including those rich in glycolic acid), polycaprolactones, biopolymers such as glycosaminoglycans, collagens, and elastin peptides, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, and mixtures of such polymers. Preferably, the biocompatible biodegradable polymer is a glycosaminoglycan or collagen.

The polymer used to form the matrix of the composition of the invention can also be non-biodegradable, so long as the polymer is biocompatible. Examples of biocompatible non-biodegradable polymers which are useful in the compositions described herein include polyethylenes, polyvinyl chlorides, polyamides such as nylons, polyesters, rayons, polypropylenes, polyacrylonitriles, acrylics, polyisoprenes, polybutadienes and polybutadiene-polyisoprene copolymers, neoprenes and nitrile rubbers, polyisobutylenes, olefinic rubbers such as ethylene-propylene rubbers, ethylene-propylene-diene monomer rubbers, and polyurethane elastomers, silicone rubbers, fluoroelastomers and fluorosilicone rubbers, homopolymers and copolymers of vinyl acetates such as ethylene vinyl acetate copolymer, homopolymers and copolymers of acrylates such as polymethylnethacrylate, polyethylmethacrylate, polymethacrylate, ethylene glycol dimethacrylate, ethylene dimethacrylate and hydroxymethyl methacrylate, polyvinylpyrrolidones, polyacrylonitrile butadienes, polycarbonates, polyamides, fluoropolymers such as polytetrafluoroethylene and polyvinyl fluoride, polystyrenes, homopolymers and copolymers of styrene acrylonitrile, cellulose acetates, homopolymers and copolymers of acrylonitrile butadiene styrene, polymethylpentenes, polysulfones, polyesters, polyimides, polyisobutylenes, polymethylstyrenes and other similar compounds known to those skilled in the art. Any one or more of these polymers can be used, for example, to coat a hydrogel matrix or a hydrogel precursor mixture, or as a support having a surface coated with a hydrogel precursor mixture or a hydrogel matrix.

Non-polymeric materials which can be used as a non-hydrogel material in the compositions described herein include any material onto an exterior surface of which a hydrogel matrix or a hydrogel precursor mixture can be covalently or non-covalently bonded, or which can be coated with or embedded in a hydrogel precursor mixture or a hydrogel matrix. Such non-polymeric materials can be biodegradable or non-biodegradable, but should be biocompatible. By way of example, useful non-polymeric materials include titanium, platinum, stainless steel, other biocompatible metal alloys, hydroxyapatite, tricalcium phosphate, cocoa butter, waxes, and ceramic materials.

Other examples of non-hydrogel materials which can be incorporated within or linked with one or more components of the hydrogel precursor mixture include agents which are capable of cross-linking components of the hydrogel precursor mixture with one another or with the virus vector. It is critical that any agent which cross-links the virus vector with the hydrogel matrix not harm the transfectiousness of the virus vector.

An important example of a non-hydrogel material which can be linked with a component of the hydrogel precursor mixture is a protein which binds specifically with the virus vector. Exemplary proteins of this type include a protein which comprises at least a complementarity-determining region of an antibody having specificity for the virus vector and a protein which comprises all or a portion of virus receptor protein with which the virus vector binds. Linkage of a protein of this type with a component of the hydrogel precursor mixture not only contributes to binding of the virus vector to the hydrogel matrix in a transfectious form, but also contributes to the stability and rigidity of the resulting composition, owing to cross-linking that occurs due to binding of proteins on different portions of the hydrogel matrix to the same virus vector particle.

Additional Components of the Composition Described Herein

Among preferred additional components for use in a hydrogel precursor mixture or a hydrogel matrix of the invention are polycations. Exemplary polycations include polylysine, polyarginine, polyomithine, polyhistidine, myelin basic protein, a low molecular weight glycopeptide, a cationic amphiphilic alpha-helical oligopeptide having a repeating sequence, a histone, a galactosylated histone, polybrene, spermine, spermidine, prolamine, polyethylenimine, putrescine, cadaverine, and hexamine. Such polycations both bind and improve the transfectiousness of virus vectors such as adenovirus vectors contained within a hydrogel matrix when a polycation is incorporated into the matrix. Polylysines consist of polypeptides of varying lengths, comprising (e.g. primarily or exclusively) lysine residues, which are positively charged at human physiological blood pH. The lysine residues can be D-lysine residues, L-lysine residues, or a mixture of the two enantiomers; poly-L-lysine is preferred. The polylysines which are useful as virus-binding agents in the compositions and methods described herein include all variants of polylysine, regardless of length, linear, branched, or cross-linked structure, conformation, isomerization, or chemical modification, that are capable of binding a virus vector in a physiologically reversible manner. Exemplary chemical modifications include methylation (Bello et al., 1985, J. Biomol. Struct. Dyn. 2:899–913) and glycosylation (Martinez-Fong et al., 1994, Hepatology 20:1602–1608). Such modifications can be made before or after synthesis of the polylysine.

Other polycations include polycationic polypeptides other than polylysines. Several amino acids are known to be positively charged at human physiological blood pH. Among the naturally occurring amino acids, lysine, arginine, and histidine are positively charged in this pH range. Other, naturally occurring and synthetic amino acids are positively charged in this pH range. Any of these amino acids can be polymerized into linear, branched, or cross-linked chains to generate polycationic polypeptides which are useful additional components in the compositions and methods described herein. Synthetic polypeptides can be produced by either chemical synthetic methods or recombinant methods. These polycationic polypeptides can be homopolymers, such as polylysine, polyarginine, polyomithine, or polyhistidine, or they can be heteropolymers, such as proteins such as myelin basic protein.

Another useful group of additional components of hydrogel matrices and hydrogel precursor mixtures described herein are proteins and ligands of protein-ligand pairs. Examples of such pairs include antibodies which bind with discrete epitopes, cell surface proteins which bind with their corresponding viral envelope proteins (e.g. HIV gp120 and CD4), and proteins which bind with non-proteinaceous compounds (e.g. biotin and an avidin such as streptavidin). If either the protein or the ligand of a protein-ligand pair is present at the exterior surface of a hydrogel matrix, then the matrix will specifically associate with a virus vector which comprises the other member of the protein-ligand pair or with a cell which comprises the other member of the protein-ligand pair. Similarly, a virus vector which comprises either the protein or the ligand of a protein-ligand pair at the exterior surface of the virus vector will specifically associate with a hydrogel matrix, a hydrogel precursor mixture, or a cell which comprises the other member of the protein-ligand pair. Thus, the compositions described herein can be targeted to a particular type of cell or tissue, or can comprise a virus vector targeted to a particular type of cell or tissue.

Implantable Devices

The compositions described herein can be used to make, to make a part of, to fill, to partially fill, to coat, or to coat at least a part of substantially any device which is to be applied to a surface of the body of an animal or which is to be inserted within the body of an animal. The implantable device can be one which is made and used for the sole purpose of delivering a composition described herein to the animal, or the device can be one which is applied to the surface of or inserted within the body of the animal for a purpose other than merely delivering a composition described herein to the animal. By way of example, the implantable device can be a bulk material or a plurality of particles which consist of the composition and which are implanted into the body animal for the sole purpose of delivering the virus vector to the animal. Further by way of example, the implantable device can be a cardiovascular stent having a surface coated with the composition; the stent is implanted within an artery of an animal both to maintain the patency of the artery and to deliver the composition to the intimal tissue of the artery or to other tissue.

The compositions and methods described herein can be used to coat virtually any medical device. The coated devices provide a convenient means for local administration of the virus vector of the composition. For example, the compositions can be used to coat degradable and non-degradable sutures, orthopedic prostheses such as supporting rod implants, joint prostheses, pins for stabilizing fractures, bone cements and ceramics, tendon reconstruction implants, ligament reconstruction implants, cartilage substitutes, prosthetic implants, cardiovascular implants such as heart valve prostheses, pacemaker components, defibrillator components, angioplasty devices, intravascular stents, acute and in-dwelling catheters, ductus arteriosus closure devices, implants deliverable by cardiac catheters such as atrial and ventricular septal defect closure devices, urologic implants such as urinary catheters and stents, neurosurgical implants such as neurosurgical shunts, ophthalmologic implants such as lens prosthesis, thin ophthalmic sutures, and corneal implants, dental prostheses, tissue scaffolds (particularly soft tissue scaffolds), internal and external wound dressings such as bandages and hernia repair meshes, and other devices and implants, as will be apparent to the skilled artisan.

In one preferred embodiment, the device having a surface coated with the composition described herein is a suture or a wound dressing, such as a bandage, a film, a mesh, or a suspension of particles, microspheres, or nanospheres. Preferably, these devices are coated with a hydrogel matrix containing a virus vector therein in a transfectious form, wherein the virus vector comprises a nucleic acid that stimulates wound healing in vivo. Sutures which can be coated in accordance with the methods and compositions described herein include any suture of natural or synthetic origin. Typical suture materials include, by way of example and not limitation, silk, cotton, linen, polyolefins such as polyethylene and polypropylene, polyesters such as polyethylene terephthalate, homopolymers and copolymers of hydroxycarboxylic acid esters, plain or chromicized collagen, plain or chromicized catgut, and suture substitutes such as cyanoacrylates. The sutures can take any convenient form such as braids or twists, and can have a wide range of sizes, such as are commonly employed in the art. Likewise, the bandages, films, and meshes can be substantially any of those presently employed as wound dressings, as well as any such dressings which are hereafter developed. The nucleic acid of the virus vector is preferably an expression construct encoding a wound healing therapeutic protein. The wound healing therapeutic protein can, for example, be selected from the group consisting of TGF-β, FGF, PDGF, PDGF-BB, IGF, M-CGF, BMP, GH, and PTE.

In another preferred embodiment of the implantable device of the invention, the hydrogel matrix described herein is used to coat one or more surfaces of a stainless steel vascular stent, and the virus vector comprises a nucleic acid selected from the group consisting of an expression construct encoding an anti-restenotic protein and an anti-restenotic antisense oligonucleotide. The expression construct can, for example, encode an anti-restenotic protein selected from the group consisting of TPA, TGF-β, FGF, Rb, p21, and TK. The anti-restenotic antisense oligonucleotide can, for example, be selected from the group consisting of a c-myb antisense oligonucleotide, a c-myc antisense oligonucleotide, and a PCNA antisense oligonucleotide.

Implantable devices such as particles, patches, and bulk materials can be fashioned from a hydrogel matrix or a hydrogel precursor mixture described herein either by making such an implantable device entirely from matrix or mixture (e.g. an implantable particle consisting of the matrix or mixture), or by separately making the implantable device and coating all or a portion thereof with the matrix or mixture (e.g. a stainless steel vascular stent having a coating comprising the matrix or mixture). When the device consists of a hydrogel matrix of the composition described herein, the device can be made by forming the device from or coating the device with a hydrogel precursor composition described herein and thereafter subjecting the device to the physiological temperature and polyvalent ion (e.g. $Ca^{2+}$) concentration of an animal in which the device is to be implanted to form a hydrogel matrix described herein. When implantable hydrogel matrix or hydrogel precursor mixture particles are made, the particles can either be synthesized as discrete particles, or the particles can be made by generating a bulk material and subsequently cutting, crushing, or grinding the bulk material to yield particles. Where bulk material comprising a hydrogel matrix or a hydrogel precursor mixture described herein is made, it is contemplated that the bulk material can be cut, shaped, sliced, or otherwise fashioned to be adapted to a cavity or other bodily structure of an animal into which the composition is to be implanted. Implantation of slices of a bulk material comprising an anti-cancer agent near the site of a brain tumor in a human patient is known (Brentt et al., 1995, J. Neurooncol. 26:111–123). By way of example, the bulk material can contain a transfectious virus vector comprising either an expression construct encoding an anti-oncogenic protein or an anti-oncogenic antisense oligonucleotide.

Methods of Making the Compositions Described Herein

To make a hydrogel matrix described herein, it is necessary to form the matrix in a manner, and using components, that will maintain the virus vector in a transfectious form. The hydrogel matrix is made by subjecting a hydrogel precursor mixture (e.g. one comprising one or more of a collagen, an alginate, and a poloxamer and a virus vector) to the physiological temperature of an animal such as a human and, optionally, to the physiological concentration in an animal such as a human of a polyvalent cation such as $Ca^{2+}$. When the mixture is subjected to these conditions, a hydrogel matrix is formed which contains the virus vector in a transfectious form. Thus, under one set of conditions corresponding to human physiological conditions, the hydrogel precursor mixture is subjected to conditions including a temperature of 37° C. and a $Ca^{2+}$ concentration of about 2.5 millimolar. The hydrogel precursor mixture can be subjected to these conditions in vitro (e.g. in a cell culture medium), or the mixture can be administered to a body location in a human, at which location, the mixture is subjected to human physiological temperature and $Ca^{2+}$ concentration, whereby a hydrogel matrix of the invention is formed.

When the hydrogel precursor mixture comprises a component that gels in the presence of cations, it can be made in the form of a single suspension comprising all of the components of the hydrogel matrix except for the polyvalent cation. Alternatively, the hydrogel precursor mixture can be made by combining dry components of the hydrogel matrix, solutions or suspensions of the components of the hydrogel matrix, a salt of a polyvalent cation, a solution comprising polyvalent cations, or some combination of these. In a preferred method, a suspension comprising type I collagen, an alginate such as sodium alginate, and a virus vector is made by suspending these components in an aqueous liquid. The proportion of collagen:alginate is preferably from about 7:3 to about 4:6. A hydrogel matrix is made by contacting this suspension with an aqueous liquid comprising 2.5 millimolar $Ca^{2+}$ at 37° C. and pH 7.4.

The duration of the period during which the polyvalent cation is contacted with the hydrogel precursor mixture is not critical. The mixture can be contacted with the polyvalent cation only momentarily, or the two can be contacted for a prolonged period of minutes, hours, days, or even weeks. It is understood however, that stiffer hydrogel matrices will be formed by contacting the hydrogel precursor mixture with higher concentrations of polyvalent cations (up to a saturating concentration) and for a longer periods (up to a maximum period, after which no further stiffening will be achieved). Furthermore, it is understood that when the hydrogel precursor mixture is a gel, or when a portion of a polyvalent cation-containing solution stiffens one portion of the hydrogel precursor mixture before contacting another portion of the hydrogel, extending the duration during which the mixture contacts the polyvalent cation-containing solution will increase the proportion of the mixture which is converted to hydrogel matrix (up to a maximum proportion, beyond which further contact does not convert any more mixture to matrix).

After contacting the hydrogel precursor mixture with the polyvalent cation-containing solution, any excess virus vector not contained within the hydrogel matrix which is formed thereby can optionally be removed from the matrix, for example by rinsing the matrix with a solvent in which the virus vector can be suspended. Alternatively, any excess vector can be left in place on the exterior surface of the matrix to provide an initial bolus of vector upon administration of the composition to an animal.

The hydrogel matrix or the hydrogel precursor mixture (when it forms a gel) can optionally be made to contain a plurality of layers of matrix or mixture, each layer optionally containing one or more virus vectors in a transfectious form. Each layer is made as described herein, another layer of matrix or mixture is deposited on the exterior surface of the previous layer of matrix or mixture. This layering process can be repeated once, twice, five times, twenty times, fifty times, or any number of times to yield a multi-layer composition. Following release of the virus vector from the exterior surface of the outermost layer of matrix or mixture, the outermost layer of matrix or mixture biodegrades, thereby exposing the exterior surface of the underlying layer, from which the virus vector can be released, after which the matrix or mixture can biodegrade, and so on. Preferably, the layers of these multi-layer compositions comprise a hydrogel matrix, rather than a hydrogel precursor mixture. Inclusion of different virus vector within various layers of matrix or mixture in these multi-layer compositions. Such compositions can be used for staged delivery of the different virus vectors.

Formation of the hydrogel matrix by injecting the hydrogel precursor mixture described herein into a body cavity of an animal is a preferred method of generating the matrix. According to this method, the hydrogel matrix is formed by contacting the hydrogel precursor mixture with the environment which is naturally located in the animal, or, alternatively, polyvalent cation can be administered to the animal in conjunction with administration of the hydrogel precursor mixture.

Methods of Delivering a Virus Vector to an Animal Cell or Tissue

The compositions described herein are useful for delivering a virus vector to an animal tissue. The virus vector can be delivered to a cell or a tissue in an animal by administering either a hydrogel precursor mixture or a hydrogel matrix described herein to the animal at a body location in fluid communication with the cell or tissue. Preferably, the mixture or matrix is administered in contact with the cell or tissue. The mixture or matrix can, for example, be in the form of implantable particles or an implantable device having a surface coated with the mixture or matrix. Upon administration of a hydrogel precursor mixture described herein to an animal, a hydrogel matrix is formed. Because the virus vector is contained within, or bound with, the matrix in a transfectious form, virus vector which is released from the matrix is in fluid communication with the cell or tissue, and is therefore capable of transfecting the cell or cells of the tissue.

Release of the virus vector from the matrix in an animal body can be effected by biodegradation of the hydrogel matrix or by physical degradation (e.g. by frictional or repeated compressive wear) of the hydrogel matrix. The hydrogel matrix is preferably biodegradable. When the hydrogel matrix is a collagen-containing hydrogel matrix, as described herein, biodegradation is believed to be attributable to the activity of one or more animal enzymes having collagenase activity. The rate at which a collagen-containing hydrogel biodegrades can therefore be regulated, for example, by changing the proportion of collagen and other component(s) (e.g. alginate or poloxamer) in the matrix. Hydrogel matrices having a higher proportion of another component will biodegrade more slowly than hydrogel matrices having a lower proportion of alginate. Furthermore, degradation of PLGA hydrogel matrices is affected, for example, by the proportions of polylactic acid substituents, which are relatively hydrophobic, and polyglycolic acid substituents, which are relatively hydrophilic in the matrix. Degradation of hydrogel matrices having an antibody linking a virus vector to the gel can depend on the identity and concentration of the antibody within the matrix.

According to this method, the composition must be placed in fluid communication with the animal tissue to which the virus vector is to be delivered. The composition, by itself or on the surface of an implantable device, can be implanted into the animal at a location at which a liquid (e.g. a body fluid such as blood, lymph, cerebrospinal fluid, a mucosal secretion, stomach or intestinal contents, or amniotic fluid) contacts both the implanted composition and the tissue to which the virus vector is to be delivered. Preferably, the composition is implanted at a body location which is geometrically close to the tissue to which delivery is desired, preferably within a few centimeters of, within a few millimeters of, or even in contact with the desired tissue.

The method of placing the composition, or a particle or device comprising the composition, in fluid communication with the tissue to which the virus vector is to be delivered is not critical. Virtually any method can be used which will result in placement of the composition in fluid communication with the tissue. By way of example, depending on the location of the tissue, the composition can be administered orally, injected, placed into an incision made in the animal body, embedded in an animal tissue (e.g. a vascular tissue undergoing balloon angioplasty) by stretching the tissue and pressing particles of the composition against the tissue, infusing the composition, sealing an incision made in the animal body using a suture, staple, or other device comprising or coated with the composition, or by applying the composition topically to an animal tissue. A preferred method of administration comprises administering a hydrogel precursor mixture described herein to a body location in an animal. The physiological temperature, the physiological polyvalent ion concentration, or both, of the animal cause a hydrogel matrix to form at the body location.

The animal tissue to which the virus vector described herein is delivered is not critical, except insofar as the identity of the tissue corresponds to the condition to be treated in the animal and the transfection capacity of the virus vector. Preferably, the tissue is a soft tissue of the animal. By way of example, prevention or amelioration of restenosis in an animal generally requires delivery of the virus vector to at least a portion of a blood vessel of the animal, and promotion of wound healing in an animal generally requires delivery of the virus vector to the wounded tissue. Of course, a virus vector capable of transfecting cells of the desired tissue should be used in the composition described herein An animal tissue can be treated either in situ (i.e. while the tissue remains a part of the animal body), or the tissue can be treated in vitro (i.e. after removing the tissue from the animal body, optionally before returning the tissue to the animal body or treating a tissue which has been cultured since removing the tissue from the animal body). Delivery of the virus vector using the compositions and methods described herein results in enhanced site-specific transfection efficiency, compared with existing virus vector delivery methods, which generally involve injection of virus vector suspended in a buffer.

The use of the hydrogel precursor mixtures and hydrogel matrices for delivery of one or more virus vectors to animal cells outside of an animal body is also contemplated. If a medium which contacts the cells is at physiological temperature, comprises a physiological concentration of a polyvalent cation, or both, then it does not matter whether the composition is a hydrogel precursor mixture or a hydrogel matrix, as the hydrogel precursor mixture will be converted to a hydrogel matrix upon contact with the medium. However, it the medium does not satisfy these conditions, then either the medium should be adjusted to meet these conditions, or the composition should be administered in the form of a hydrogel matrix.

It is known that diabetic patients experience impaired wound healing ability, relative to non-diabetic patients. In one contemplated virus vector delivery method, a hydrogel precursor mixture or a hydrogel matrix is used to deliver a virus vector which comprises an expression construct encoding a wound healing therapeutic protein to a wounded tissue of an animal such as a diabetic human patient. For example, the wound healing therapeutic protein can be PDGF-BB. The mixture or matrix can, for example, be administered to the patient in the form of particles, bulk material, or film comprising an adenovirus vector which comprises the expression vector. The mixture or matrix is administered directly to the site of the wound. If the wound is at the surface of the patient's body, the mixture or matrix can, for example, be administered topically in the form of a wound dressing coated with the mixture or matrix or in the form of a suspension of particles consisting of the mixture or matrix. If the wound is beneath the patient's skin, the mixture or matrix can, for example, be administered by injection of a suspension of particles of the mixture or matrix or of a bulk material into the site of the wound, or by making an incision in the patient's skin to expose the wound site and then topically administering the mixture or matrix to the wound site. Advantageously, an animal model exists which can be used to optimize the mixture or matrix prior to administering the composition to a human patient. Db/db (diabetic) mice exhibit wound healing impairment which is characteristic of the. wound healing impairment exhibited by human diabetic patients (Igel et al., July, 1996, Diabetologia 39:758–765). Methods of making db/db mice have been described (Prochazka et al., 1986, Diabetes 35:725–728). Use of this animal model to optimize a composition of the invention is described herein in Example 4.

Delivery of therapeutic compounds to ischemic tissues can be hindered by the limited blood supply which, by definition, is provided to ischemic tissues. In another contemplated virus vector delivery method, a hydrogel precursor mixture or a hydrogel matrix described herein is used to deliver a virus vector to cells of an ischemic tissue in an animal such as a human patient. A mixture or matrix described herein is administered directly to an ischemic tissue site in the animal in order to deliver a virus vector, such as one which comprises or contains a nucleic acid encoding an angiogenic factor (e.g. FGF or VEGF{vascular endothelial growth factor}). Advantageously, an animal model exists which can be used to optimize the composition prior to administering the mixture or matrix to a human patient A rabbit ear model of ischemic has been described, wherein the ischemic tissue in the rabbit ear model exhibits the characteristics of human ischemic tissue (Zhao et al., 1994, Arch. Surgery 129:1043–1049; Pierce et al., 1991, Am. J. Pathol. 138:629–646). Use of this animal model to optimize a composition of the invention is described herein in Example 5.

It is known that wounds in gastrointestinal tissues are slow to heal and that complications related to such wounds frequently develop. Reconstructive surgery involving gastrointestinal tissues is frequently necessary in patients afflicted with intestinal or colon cancers, colitis, or congenital malformations. In yet another contemplated virus vector delivery method, a hydrogel precursor mixture or a hydrogel matrix described herein is administered intraluminally, periadventitially, or both, to an injured gastrointestinal tissue in an animal such as a human patient. Preferably, the virus vector of the composition comprises or contains a nucleic acid encoding, for example, at least one of PDGF, TGF-$\beta$, and FGF. Advantageously, an animal model exists which can be used to optimize the composition prior to administering the mixture or matrix to a human patient. A rat ischemic intestinal anastomosis model of wounded gastrointestinal tissue has been described, wherein the intentionally wounded gastrointestinal tissue in the rat model exhibits the characteristics of wounded human gastrointestinal tissue (Hogstrom et al., 1986, Surgery 99:716–720). Use of this animal model to optimize the composition of the invention is described herein in Example 6.

The desirability of effective in utero gene therapy methods cannot be underestimated. Effective in utero gene therapy can be used to cure or alleviate genetically-based disease prior to the birth of the patient afflicted with the disease, thereby precluding significant discomfort or suffering. In still other contemplated virus vector delivery methods, a hydrogel precursor mixture or a hydrogel matrix described herein is administered in utero to an embryo or fetus of an animal such as a human. Such methods can have two goals: to induce immune tolerization of the animal toward the virus vector and/or to deliver a therapeutic composition to the animal in utero. Induction of immune tolerance toward the virus vector in utero permits the virus vector to be used for gene therapy of the animal without inducing an immune response toward the vector. The gene therapy can be performed while the animal is in utero or later in the animal's life, such as during the animal's adult life. In utero gene therapy methods have been described (e.g. Flake et al., 1996, N. Engl. J. Med. 335:1806–1810). In one embodiment of an in utero gene therapy method, a virus vector comprising a normal copy of the CFTR gene is delivered to airway cells of a fetus or embryo diagnosed as having one or more abnormal copies of this gene. It is understood, however, that virtually any localized congenital malformation could be favorably treated in utero using the site-specific viral hydrogel gene delivery methods described herein.

Advantageously, an animal model exists which can be used to optimize the composition prior to administering the mixture or matrix to a human patient. Administration of a composition described herein to a sheep in utero in order to effect immune tolerization of the sheep to the virus vector can be used as a model of immune tolerization of human embryos and fetuses in utero. Use of this animal model to optimize the composition is described herein in Example 7.

The invention encompasses the preparation and use of pharmaceutical compositions comprising a hydrogel precursor mixture or a hydrogel matrix described herein. Such a pharmaceutical composition can consist of the composition alone, in a form suitable for administration to a subject, or the pharmaceutical composition can comprise the composition or a particle or device coated with the composition combined with one or more pharmaceutically acceptable carriers, one or more additional ingredients, or some combination of these. Administration of one of these pharmaceutical compositions to a subject is useful for delivering the virus vector to the subject, as described elsewhere in the present disclosure.

As used herein, the term "pharmaceutically acceptable carrier" means a chemical composition with which a hydrogel precursor mixture or matrix of the invention can be combined and which, following the combination, can be used to administer the virus vector to a subject.

The formulations of the pharmaceutical compositions described herein can be prepared by any method known or hereafter developed in the art of pharmacology. In general, such preparatory methods include the step of bringing a hydrogel precursor mixture or matrix of the invention into association with a carrier (e.g. water or phosphate-buffered saline) or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions is contemplated include humans and other primates, mammals including commercially relevant mammals such as cattle, pigs, horses, sheep, cats, and dogs, birds including commercially relevant birds such as chickens, ducks, geese, and turkeys, fish including farm-raised fish and aquarium fish, and crustaceans such as farm-raised shellfish.

Pharmaceutical compositions that are useful in the methods described herein can be prepared, packaged, or sold in formulations suitable for oral, rectal, vaginal, parenteral, topical, pulmonary, intranasal, buccal, ophthalmic, or another route of administration. Other contemplated formulations include microspheres, nanospheres, projected nanoparticles, liposomal preparations, resealed erythrocytes comprising the composition, and immunologically-based formulations.

A pharmaceutical composition can be prepared, packaged, or sold in bulk, as a single unit dose, or as a plurality of single unit doses. As used herein, a "unit dose" is discrete amount of the pharmaceutical composition comprising a predetermined amount of a hydrogel precursor mixture or matrix described herein. The amount of the mixture or matrix is generally equal to an amount which contains a desirable dosage or amount of the virus vector for delivery to the subject or a convenient fraction of such a dosage such as one-half or one-third of such a dosage.

The relative amounts of the mixture or matrix, the pharmaceutically acceptable carrier, and any additional ingredients in a pharmaceutical composition will vary, depending upon the identity, size, and condition of the subject treated and further depending upon the route by which the composition is to be administered. By way of example, the composition of the invention can comprise between 0.1% and 100% (w/w) of the pharmaceutical composition.

In addition to the mixture or matrix of the invention, a pharmaceutical composition can further comprise one or more additional pharmaceutically active agents. Particularly contemplated additional agents include agents for enhancing gene transfection such as lysosomotropic agents of low molecular weight (e.g. sucrose) and inducers or activators of specific promoters (e.g. tetracycline sensitive promoters).

A formulation of a pharmaceutical composition suitable for oral administration can be prepared, packaged, or sold in the form of a discrete solid dose unit including a tablet, a hard or soft capsule, a cachet, a troche, or a lozenge, each containing a predetermined amount of the mixture or matrix of the invention or a predetermined amount of the virus vector described herein. Other formulations suitable for oral administration include a powdered or granular formulation, an aqueous or oily suspension, or an emulsion.

As used herein, an "oily" liquid is one which comprises a carboncontaining liquid molecule and which exhibits a less polar character than water.

A tablet comprising the mixture or matrix described herein can, for example, be made by compressing or molding the composition, optionally with one or more additional ingredients. Compressed tablets can be prepared by compressing, in a suitable device, the mixture or matrix in a free-flowing form such as a microspherical or nanospherical powder or granular preparation, optionally mixed with one or more of a binder, a lubricant, an excipient, a surface active agent, and a dispersing agent. Molded tablets can be made by molding, in a suitable device, a mixture of the mixture or matrix, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a subject, thereby providing sustained release of the composition described herein. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the composition described herein can be made using a physiologically degradable composition, such as gelatin. Such hard capsules comprise the mixture or matrix, and can further comprise additional ingredients including, for example, an inert solid diluent such as calcium carbonate, calcium phosphate, or kaolin.

Soft gelatin capsules comprising the composition described herein can be made using a physiologically degradable composition, such as gelatin. Such hard capsules comprise the mixture or matrix, which can be mixed with water or an oil medium such as peanut oil, liquid paraffin, or olive oil.

Liquid suspensions of a pharmaceutical composition described herein which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the mixture or matrix described herein in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including suspending agents, dispersing or wetting agents, emulsifying agents, demulcents, preservatives, buffers, salts, flavorings, coloring agents, and sweetening agents. Oily suspensions can further comprise a thickening agent. Known suspending agents include sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include naturally-occurring phosphatides such as lecithin, condensation products of an alkylene ioxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Powdered and granular formulations of a pharmaceutical preparation can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition can be prepared, packaged, or sold in a formulation suitable for rectal administration. Such a composition can be in the form of, for example, a suppository, a retention enema preparation, and a suspension for rectal or colonic irrigation.

Suppository formulations can be made by combining the composition described herein with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include cocoa butter, polyethylene glycols, and various glycerides. Suppository formulations can further comprise various additional ingredients including antioxidants and preservatives.

Retention enema preparations or suspensions for rectal or colonic irrigation can be made by combining the composition described herein with a pharmaceutically acceptable liquid carrier. As is known in the art, enema preparations can be administered using, and can be packaged within, a delivery device adapted to the rectal anatomy of the subject. Enema preparations can further comprise various additional ingredients including antioxidants and preservatives.

A pharmaceutical composition can be prepared, packaged, or sold in a formulation suitable for vaginal administration. Such a composition can be in the form of, for example, a suppository, an impregnated or coated vaginally-insertable material such as a tampon, a douche suspension, or a suspension for vaginal irrigation.

Methods for impregnating or coating a material with a chemical composition are known in the art, and include methods of depositing or binding a chemical composition onto a surface, methods of incorporating a chemical composition into the structure of a material during the synthesis of the material (i.e. such as with a physiologically degradable material), and methods of absorbing an aqueous or oily suspension into an absorbent material, with or without subsequent drying.

Douche preparations or suspensions for vaginal irrigation can be made by combining the mixture or matrix described herein with a pharmaceutically acceptable liquid carrier. As is known in the art, douche preparations can be administered using, and can be packaged within, a delivery device adapted to the vaginal anatomy of the subject. Douche preparations can further comprise various additional ingredients including antioxidants, antibiotics, antifungal agents, and preservatives.

Vaginal preparations of the composition described herein can also be used for administration in utero of the virus vector described herein to an ovum, embryo, fetus, or to a neonate during birth. Such preparations are preferably placed in the uterus of the woman bearing the ovum, embryo, fetus, or neonate, although such preparations can also be placed cervically or vaginally or can be physically contacted with the embryo or fetus or on or within the chorionic or amniotic membranes.

As used herein, "parenteral administration" of a pharmaceutical composition includes any route of administration characterized by physical breaching of a tissue of a subject and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, by application using a device (e.g. a balloon angiocatheter) inserted at one site in a blood vessel of an animal and physically urged along the vessel to a second site in the blood vessel of the animal, by administration of the composition using a wound dressing (e.g. a bandage, a suture, or a hernia repair mesh) comprising the pharmaceutical composition, and the like. In particular, parenteral administration is contemplated to include subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the mixture or matrix described herein combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include suspensions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. microspherical or nanospherical powder or granular) form for reconstitution with a suitable vehicle (e.g. sterile pyrogen-free water) prior to parenteral administration of the reconstituted composition. Use of a doubleballoon or 'sweating' balloon type of angiocatheter to deliver a pharmaceutical composition described herein to the intimal surface of a blood vessel of an animal is contemplated. Also contemplated is delivery of the virus vector described herein using a pharmaceutical composition comprising a wound dressing which comprises the mixture or matrix described herein.

Preferred compositions for parenteral administration comprise a hydrogel precursor mixture which, when administered to a body location such as a location within a human body or to an environment having a temperature (e.g. 37° C.) and polyvalent cation concentration (e.g. $[Ca^{2+}]=2.5$ millimolar) similar to those of a body location stiffen to form a hydrogel matrix.

The pharmaceutical compositions can be prepared, packaged, or sold in the form of a sterile injectable aqueous or oily suspension. This suspension can be formulated according to the known art, and can comprise, in addition to the composition described herein, additional ingredients such as the dispersing agents, wetting agents, or suspending agents described herein. Such sterile injectable formulations can be prepared using a non-toxic parenterally-acceptable diluent or solvent, such as water or 1,3-butane diol, for example. Other acceptable diluents and solvents include Ringer's solution, isotonic sodium chloride solution, and fixed oils such as synthetic mono- or di-glycerides. Other parentally-administrable formulations which are useful include those which comprise the mixture or matrix of the invention in bulk form, in particulate form, in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 1% to about 10% (w/w) of the mixture or matrix, although the concentration of the mixture or matrix in the solvent of the formulation can be higher. Formulations for topical administration can further comprise one or more of the additional ingredients described herein. Preferably, the mixture or matrix is in a microspherical or nanospherical form when it is used to generate a pharmaceutical composition for topical administration, as these forms can be more efficiently taken up by animal tissues.

A pharmaceutical composition can be prepared, packaged, or sold in a formulation suitable for pulmonary administration via the buccal cavity. Such a formulation can comprise dry particles which comprise, which consist of, or which are coated with the mixture or matrix described herein and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the mixture or matrix described herein dissolved or suspended in a biocompatible, low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant can constitute 50 to 99.9% (w/w) of the pharmaceutical composition, and the composition can constitute 0.1 to 20% (w/w) of the pharmaceutical composition. The propellant can further comprise additional ingredients such as a liquid non-ionic or solid anionic surfactant or a solid diluent (preferably having a particle size of the same order as particles comprising the active ingredient).

Pharmaceutical compositions formulated for pulmonary delivery can also provide the composition described herein in the form of droplets of a suspension of the composition. Such formulations can be prepared, packaged, or sold as aqueous or dilute alcoholic suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition.

Another formulation suitable for intranasal administration is a coarse powder comprising the mixture or matrix described herein and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration can, for example, comprise from about as little as 0.1% (w/w) and as much as 100% (w/w) of the mixture or matrix described herein, and can further comprise one or more of the additional ingredients described herein.

A pharmaceutical composition can be prepared, packaged, or sold in a formulation suitable for buccal administration. Such formulations can, for example, be in the form of tablets or lozenges made using conventional methods, and can, for example, 0.1 to 20% (w/w) of the mixture or matrix described herein, the balance comprising an orally dissolvable or degradable composition and, optionally, one or more of the additional ingredients described herein. Alternatively, formulations suitable for buccal administration can comprise a powder or an aerosolized or atomized suspension comprising the mixture or matrix. Such powdered, aerosolized, or aerosolized formulations, when dispersed, preferably have an average particle or droplet size in the range from about 0.1 to about 200 nanometers, and can further comprise one or more of the additional ingredients described herein.

A pharmaceutical composition can be prepared, packaged, or sold in a formulation suitable for ophthalmic administration. Such formulations can, for example, be in the form of eye drops including, for example, a 0.1–1.0% (w/w) suspension of the mixture or matrix described herein in an aqueous or oily liquid carrier. Such drops can further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which can be included in the pharmaceutical compositions are known in the art and described, for example in Genaro, ed., 1985*, Remington's Pharmaceutical Sciences*, Mack Publishing Co., Easton, Pa., which is incorporated herein by reference.

It is understood that the ordinarily skilled physician or veterinarian will determine and prescribe an effective amount of the composition described herein for delivery to the subject. In so proceeding, the physician or veterinarian can, for example, prescribe a relatively low dose at first, subsequently increasing the dose until an appropriate response is obtained. It is further understood, however, that the specific dose level for any particular subject will depend upon a variety of factors including the identity of the virus vector described herein, the identity and properties of the nucleic acid carried by the virus vector, the estimated efficiency of uptake of the virus vector by the subject, the age, body weight, general health, gender, and diet of the subject, the time of administration, the route of administration, the rate of excretion, any drug combination, and the severity of the condition being treated.

The Kits of the Invention

The invention includes a variety of kits which are useful for making and using the compositions described herein.

In one embodiment of a kit of the invention, the kit comprises a hydrogel precursor mixture and an instructional material which describes a method of making a hydrogel matrix containing a virus vector therein in a transfectious form. By way of example, the mixture can comprise a collagen, an alginate, or preferably both, either in a dried or concentrated suspension or in a suspension containing the compound(s) at the concentration at which they are to be used to form the matrix. The hydrogel precursor mixture can further comprise one or more of the additional matrix components described herein. Alternatively, or in addition, the instructional material can describe how to use the composition described herein to deliver a virus vector to an animal tissue. The kit can optionally comprise one or more of the virus vector described herein, a virus vector precursor, a container or coating in which the hydrogel matrix described herein can be formed, and a solvent in which one or more components of the hydrogel precursor mixture described herein can be dissolved or suspended. When the kit comprises a virus vector precursor, the precursor is preferably an adenovirus vector comprising a nucleic acid having a multiple restriction site.

In an alternative embodiment, the kit comprises the composition described herein and one or more of an instructional material for administering the composition to an animal tissue, a device for administering the composition to an animal tissue, and a pharmaceutical carrier for combination with the composition prior to administering the composition to an animal tissue.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, a "virus vector" is a nucleic acid-containing composition which comprises a protein which naturally occurs in a virus, wherein the composition is capable of transferring its nucleic acid into the interior of at least one type of cell when the virus vector is contacted with the cell.

A "virus vector precursor" is a virus vector into which a nucleic acid can be introduced using a known method. For example, a virus vector precursor comprising a nucleic acid having a multiple restriction site enables a user to create a virus vector of interest by inserting a nucleic acid of interest at the multiple restriction site.

A virus vector is in a "transfectious" form if the virus vector is able to bind specifically with a cell and to transfer a nucleic acid of the vector to the interior of the cell.

"Staged delivery" of a first and a second virus vector means transfection of cells with the first virus vector at a time when the cells are not transfected with the second virus vector, followed by transfection of cells with the second virus vector at a later time.

A virus vector is "contained within" a hydrogel if the virus vector is not substantially released from the hydrogel by diffusion in the absence of hydrogel degradation.

A "transfection indicator" is a component of a virus vector which, when transferred to a cell by the virus vector, confers an observable phenotype to the cell. A non-limiting example of a transfection indicator is a β-galactosidase gene operably linked to a promoter.

By "nucleic acid" is meant any homopolymer or heteropolymer of deoxyribonucleosides, ribonucleosides, or nucleoside analogs. The nucleotide analogs can be any compound known in the art to be or subsequently discovered to be useful as a structural analog of a ribonucleoside or a deoxyribonucleoside. Nucleotide analogs include nucleotides comprising bases other than the five biologically occurring bases (adenine, guanine, thymine, cytosine and uracil). The monomers of the nucleic acid can be connected by phosphodiester linkages or modified linkages such as phosphotriester, phosphoramidate, siloxane, carbonate, carboxymethyl ester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages.

A nucleic acid "expression construct" is a nucleic acid which encodes an RNA or protein product which is formed upon transcription or upon transcription and translation, respectively, of the nucleic acid. RNA expression constructs which can be directly translated to generate a protein product, or which can be reverse transcribed and either transcribed or transcribed and translated to generate an RNA or protein product, respectively, are also included within this definition.

A "transcribable construct" is a DNA molecule having a transcriptional start site and any promoter/regulatory sequence which is necessary to enable an RNA molecule to be generated by transcription thereof or an RNA molecule having any promoter/regulatory sequence which is necessary to enable generation of a DNA molecule by reverse transcription thereof.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "promoter/regulatory sequence" means a nucleic acid sequence which is required for expression of a gene product operably linked to the promoter/regulator sequence. In some instances, this sequence can be the core promoter sequence and in other instances, this sequence can also include an enhancer sequence and other regulatory elements which are required for expression of the gene product. The promoter/regulatory sequence can, for example, be one which expresses the gene product in a tissue specific manner.

A "ribozyme" is an RNA molecule, or a molecule comprising an RNA molecule and a polypeptide molecule, which is capable of specifically catalyzing a chemical reaction, in a manner analogous to enzymatic catalysis.

An "antisense oligonucleotide" is a nucleic acid molecule (e.g. DNA, RNA, or a polymer comprising one or more nucleotide analogs), at least a portion of which is complementary to a nucleic acid which is present in a cell. The antisense oligonucleotides preferably comprise between about twelve and about fifty nucleotides. More preferably, the antisense oligonucleotides comprise between about fourteen and about thirty nucleotides. Most preferably, the antisense oligonucleotides comprise between about sixteen and about twenty-one nucleotides. The antisense oligonucleotides include phosphorothioate oligonucleotides and other modifications of oligonucleotides, as described herein. Methods for synthesizing oligonucleotides, phosphorothioate oligonucleotides, and otherwise modified oligonucleotides are known in the art (U.S. Pat. No: 5,034,506; Nielsen et al., 1991, Science 254: 1497), and each of these types of modified oligonucleotides in included within the scope of the invention.

A "therapeutic protein" is a protein which, when provided to or expressed in a diseased or wounded tissue, alleviates, prevents, or inhibits the disease, promotes healing of the wound, or prevents worsening of the wound.

A "viral genome fragment" means at least a portion of a nucleic acid which is a component of a naturally-occurring virus.

A "gene fragment" means at least a portion of a nucleic acid which, alone or in conjunction with other operably linked nucleic acids, constitutes a gene.

A hydrogel matrix "stiffens" if the bulk rigidity of the matrix increases. For example, a stiffened hydrogel matrix retains its shape in conditions in which a non-stiffened hydrogel matrix would not.

The "exterior surface" of a matrix, device, particle, or surface is the surface or portion of a surface which contacts a solvent in which the matrix, device, particle, or surface is immersed.

The "interior portion" of a matrix is a portion of the matrix which does not contact a solvent in which the matrix is suspended or in which a device or particle coated with the matrix is suspended or immersed, at least until the matrix has at least partially biodegraded. It is understood that, in instances in which multiple layers of matrix are present, the "interior portion(s)" of the matrix can refer only to the innermost portion of the innermost layer of the matrix (i.e. the first-deposited layer) or to the inner portion of each layer of the matrix, with respect to the first-deposited layer. The interior portion of the matrix does not include the exterior surface of the matrix, but can include any and all parts of the matrix that are not exposed on the exterior surface.

A material is "biocompatible" with respect to an animal if the presence of the material in the animal is not injurious to the animal. By way of example, a biocompatible material does not induce an immune response to the material when the material is implanted in the body of an animal.

A material is "biodegradable" if the material undergoes decomposition when contacted with a biological system such upon implantation into an animal. The decomposition can be evidenced, for example, by dissolution, depolymerization, disintegration, or by another chemical or physical change whereby the bulk of the material in the biological system is reduced over time. Such decomposition can be, but is not necessarily, catalyzed by a component of the biological system (e.g. an enzyme).

A material is administered "in fluid communication" with a tissue if the material is administered to a location which contacts a fluid which normally contacts the tissue, either in vitro or in vivo. Examples of administration of a material in fluid communication with a tissue include deposition, suspension, or dissolution of a material in a tissue culture medium in which the tissue is maintained, deposition, suspension, or dissolution of a material in a body fluid which normally contacts the tissue in an animal, and administration of a material such that it physically contacts the tissue. For the purposes of the present disclosure, embryonic and fetal tissues are considered to be "in fluid communication" with materials which physically contact the embryo or fetus, with materials which are deposited, suspended, or dissolved in amniotic fluid which surrounds the embryo or fetus, and with materials which are deposited, suspended, or dissolved in uteral, cervical, or vaginal fluids of an animal which bears the embryo or fetus.

A "soft tissue" means a tissue which does not primarily consist of one or more precipitated inorganic minerals. By way of example, mammalian bones and teeth primarily consist of a variety of precipitated inorganic minerals, and are not soft tissues.

A device, particle, or surface is "coated" with a material if at least a part of a surface of the device or particle or at least a part of the surface has the material present at the exterior surface thereof.

A "protein-ligand pair" refers to a protein and another molecule, wherein the protein specifically binds with the other molecule. Examples of protein-ligand pairs include an antibody and its corresponding epitope and an avidin protein, such as streptavidin, and biotin.

A "cell-specific oligosaccharide" means a polysaccharide which binds specifically with a ligand which is normally located on the surface of cells of an identifiable type.

A "particle" or "particulate formulation" of a hydrogel matrix means a hydrogel matrix having geometric dimensions compatible with injection, cellular ingestion, or mucous membrane penetration. Thus, such a hydrogel matrix typically comprises, or preferably consists essentially of, spherical or ellipsoid particles having a maximal geometric dimension of about 50 microns, preferably less Man about one micron, and more preferably, from about 100 nanometers to 500 nanometers.

A "bulk material" or "bulk formulation" of a hydrogel matrix means a monolithic hydrogel matrix, having geometric dimensions in excess of those compatible with injection, cellular ingestion, or mucous membrane penetration. Such bulk formulations typically have one or more geometric dimensions in excess of 50 microns in diameter. Bulk materials can, for example, be provided in the form of spheres, irregular shapes, sheets, needles, bars, and the like.

The "hydrodynamic diameter" of an object such as a molecule or a particle refers to the diameter of an imaginary sphere which is traced by rotating the object in all directions around its center of mass. The hydrodynamic diameter can be thought of roughly as the 'effective size' of an object rotating rapidly in space or in solution. By way of example, the hydrodynamic diameter of a sphere is the actual diameter of the sphere, and the hydrodynamic diameter of a rigid rod-shaped object is the length of the object along its longest axis (i.e. the length of the rod).

An "implantable device" means a particle or other object which can be entirely or partially inserted into the body of an animal. Implantable devices thus include particles which, when applied topically to a surface of the animal body, are capable of being taken up by a tissue or cell of the animal. The means by which the particle or other object is inserted into the animal body is not critical, and includes, for example, swallowing, inhalation, injection, topical application, physical penetration, insertion into an incision made in the animal body, and the like.

A "wound healing therapeutic protein" is a protein which, when provided to a wounded tissue in an animal, promotes healing of the wounded tissue.

An "anti-restenotic protein" is a protein which, when provided to the site of an intimal vascular injury (e.g. following performance of a balloon angioplasty procedure at the site), prevents, inhibits, or alleviates restenotic injury at the site. The anti-restenotic protein can, for example, prevent migration of smooth muscle or other cells to the site, prevent proliferation of smooth muscle or other cells at the site, or cause smooth muscle or other cells to dissociate from the site.

An "anti-restenotic antisense oligonucleotide" is an antisense oligonucleotide which, when provided to the site of an intimal vascular injury, prevents, inhibits, or alleviates restenotic injury at the site.

An "oncogene" as used herein, includes both genes which are identified in the art as oncogenes and those which are identified as tumor suppressor genes. A distinguishing characteristic of both oncogenes and tumor suppressor genes is their association with control of the processes of oncogenesis, metastasis, or apoptosis.

An "anti-oncogenic protein" is a protein, such as a protein encoded by an oncogene, which, when provided to the site of a cancerous or pre-cancerous lesion in an animal, prevents, inhibits, or reverses abnormal cellular growth at the site or induces apoptosis of cells of the lesion.

An "anti-oncogenic antisense oligonucleotide" is an antisense oligonucleotide which, when provided to the site of cancerous or pre-cancerous lesion in an animal, prevents, inhibits, or reverses abnormal cellular growth at the site or induces apoptosis of cells of the lesion.

An "imaging agent" is a chemical compound which, when administered to an animal, permits or eases observation of a cell, tissue, cavity, organ, or another physiological structure of the animal.

As used herein, an "instructional material" includes a publication, a recording, a diagram, or any other medium of expression which can be used to communicate the usefulness of the composition described herein for delivering a virus vector according to the methods described herein or which can be used to communicate a method of making or using a composition as described herein. The instructional material can, for example, be affixed to a container which contains the composition or be shipped together with a container which contains the composition. Alternatively, the instructional material can be shipped separately from the container with the intention that the instructional material and the composition be used cooperatively by the recipient.

The hydrogel matrix composition described herein can also be used as a storage of a virus vector in a transfectious form for an extended period (i.e. days, weeks, months, or even longer). This composition is made by combining the hydrogel precursor mixture described herein with the virus vector, and then contacting the mixture with polyvalent ions, such as calcium ions (e.g. at a concentration of at least about 100 micromolar, and preferably at a concentration of about 1 millimolar or higher), subjecting the composition to the physiological temperature of a mammal (e.g. 37° C.), or both. The precursor mixture, polyvalent ions, and virus vector can, for example, be combined within a storage vessel such as a bottle, capsule, or other known container. Stored in this form, the virus vector will remain transfectious for a much longer period than if the virus vector were stored in a suspension or lyophilized form, such as for a period of days, weeks, months, or even longer.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

EXAMPLE 1

In this Example, a method of preparing a composition of the invention is described. This composition comprised an adenovirus vector suspended in a hydrogel precursor mixture.

The hydrogel precursor mixture was made by combining a suspension of bovine type I collagen, a suspension of sodium alginate, and a suspension of a type 5 adenovirus vector which comprised an expression construct encoding an *Escherichia coli* β-galactosidase gene (lacZ). The mixture comprised, on a dry weight basis, 70% type I collagen and 30% alginate, and the mixture was prepared at pH 7.4. Phosphate buffered saline having the virus, collagen, and alginate suspended therein was prepared by gentle swirling of a container containing these ingredients prior to gelation. At 37° C., the hydrogel precursor mixture formed a firm gel in the absence of calcium ions. However, it was observed that the physical handling strength (i.e. stiffness) of the mixture was considerably improved by exposing the gel to a physiologic calcium concentration (i.e. 2.5 millimolar $Ca^{2+}$). The mixture, as well as the hydrogel matrix formed after contacting the mixture with $Ca^{2+}$, comprised about $10^{10}$ plaque-forming units of the virus vector per 200 milliliter of mixture or matrix. A total of about 350 nanograms of DNA was used in these experiments.

A fluorescence assay was used to assess in vitro release of the virus vector from the hydrogel matrix. This assay involved measuring fluorescence attributable to complexation of thiazole orange, an intercalating agent, into the DNA of the adenovirus vector, as described (Walter, 1995, J. Molec. Biol. 254:856–868). When the hydrogel matrix was incubated in 50 millimolar Tris buffer (pH 7.4) containing 50 millimolar EDTA, very little vector was released from the matrix, as demonstrated by the open squares in FIG. 1. However, addition to the medium of a clostridial collagenase enzyme resulted in significant release of the adenovirus vector from the matrix. The rate of release of the virus vector from the matrix was approximately proportional to the amount of collagenase present in the buffer, as indicated in FIG. 1.

EXAMPLE 2

The experiments described in this Example demonstrated that a hydrogel matrix which contained a virus vector comprising an expression construct was capable of delivering the virus vector to cells with which the matrix was in contact and to cells which were in fluid communication with the matrix.

Primary neonatal human fibroblasts were incubated with the collagen-alginate hydrogel matrix described in Example 1, which contained the type 5 adenovirus vector described in that example.

Figure 2A:
FIGS. 2A, 2B, 2C, 2D, and 2E, is a series of images which depict cultured human neonatal fibroblasts to which a collagen alginate hydrogel composition described herein comprising an adenovirus vector was delivered. The virus vector comprised an expression vector encoding β-galactosidase, and the cells were stained by exposing them to X-gal prior to production of the images. The cells depicted in FIGS. 2A, 2B, and 2C were incubated for four days (FIG. 2A), eight days (FIG. 2B), or twelve days (FIG. 2C) in medium to which a freshly prepared hydrogel was added. The cells depicted in FIGS. 2D and 2E were incubated for four days (FIG. 2D) or eight days (FIG. 2E) in medium to which a hydrogel which had been maintained at room temperature for two weeks prior to adding the hydrogel to the medium.
Figure 2B:
Figure 2C:

In one set of experiments, the hydrogel matrix was contacted with the cells. While the cells were incubated in contact with the hydrogel matrix, they continuously expressed the β-galactosidase gene of the vector for more than three weeks. Images of cells which were incubated geometrically beneath the suspended hydrogel matrix for four, eight, and twelve days are presented in FIGS. 2A, 2B, and 2C, respectively.

In another set of experiments, the hydrogel was suspended above the surface of cultured fibroblasts, without touching the surface of the cells. After twentyfour hours of incubation, only a single transfected cell was observed on the surface of the plate. However, after three days of incubation, thirty percent of the cells on the plate had been transfected by the virus vector. These results suggested that release of the virus vector from the hydrogel matrix was attributable to the presence in the medium of an enzyme having collagenase activity which was secreted by the cells.

Figure 2D:
Figure 2E:
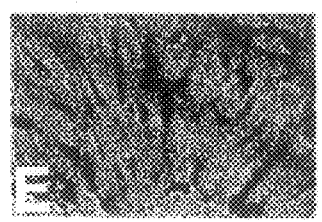

In order to assess the stability of the transfectious state of the virus vector contained within the hydrogel matrix, the matrix containing the vector was stored at room temperature (i.e. about 20° C.) for two weeks. Fibroblasts which were incubated geometrically beneath the hydrogel matrix following storage of the matrix were transfected at an efficiency approximately equal to that of fibroblasts incubated with freshly prepared hydrogel matrix, as indicated by the images of FIGS. 2D and 2E.

EXAMPLE 3

In the experiments described in this Example, a method of making a composition for controlled delivery of a virus vector according to the methods of the present invention is described. A method of characterizing the composition is also described.

A hydrogel precursor mixture is formed by combining a suspension of bovine type I collagen (available, e.g., from Collagen Corporation, Fremont, Calif.) with a suspension of sodium alginate and a suspension of a virus vector. The virus vector can, for example, be a type 5 adenovirus vector comprising an expression construct which encodes either a wound healing therapeutic protein such as PDGF-BB or a protein which can be easily assayed, such as β-galactosidase. The proportion of collagen:alginate, on a dry weigh basis, can be from about 7:3 to about 4:6. After forming the hydrogen precursor mixture, a hydrogel matrix is formed therefrom by solidifying the mixture. The mixture can be solidified by contacting it with polyvalent cations such as $Ca^{2+}$. Preferably, the mixture is contacted with an aqueous solution comprising at least about 2.5 millimolar $Ca^{2+}$.

Nanoparticles comprising fluorescent particles and virus vectorcontaining nanoparticles are examined to determine in vitro release virus vector or fluorescent particles from the hydrogel matrix under simulated physiologic conditions, for example in a buffer having a pH of 7.4 and a temperature of 37° C. Release of the vector from the hydrogel matrix is assessed both in the presence of collagenase (e.g. a clostridial collagenase enzyme) and in buffer not comprising collagenase.

Biophysical parameters of the hydrogel matrix are also assessed. Relevant parameters of the hydrogel matrices include the structural integrity (e.g. the glass transition temperature) of the matrix, which can be assessed using known techniques including Fourier transform infrared spectroscopy and differential scanning calorimetry. The results obtained using the experimental procedures described in the Example can be used to optimize the characteristics of the composition in light of the virus vector to be used and the cells to which the virus vector is to be delivered or the body location to which the composition is to be administered.

EXAMPLE 4

The methods described in this Example relate to an experimental procedure for assessing the usefulness of a composition of the invention for delivering a virus vector to wounded tissue of an animal for the purpose of promoting wound healing.

In these methods, diabetic mice are used as a model for virus vector delivery to excision-wounded tissue for the purpose of promoting healing of the tissue. The diabetic mice which are used are db/db (diabetic) mice, such as those described in Prochazka et al. (1986, Diabetes 35:725–728). Excision wounding was performed by excising a piece of skin from each mouse. Such mice exhibit impaired excisional wound healing ability, relative to normal mice. Excisional wounds are made upon individual db/db mice. A hydrogel matrix, or a hydrogel precursor mixture, comprising a virus vector is topically administered at the surface of the wound. The virus vector can comprise an expression construct which encodes a wound healing protein (e.g. a recombinant, replication-defective adenovirus comprising an expression construct encoding PDGF-BB) or some other transfection indicator, such as an expression construct encoding β-galactosidase. The same matrix or mixture, not comprising the virus vector, is topically applied to the wounds of the remaining (i.e. control) mice. Preferably, groups of 10 mice are compared. Excision wounded db/db mice can also be injected with the virus vector in order to compare the efficiency of virus vector delivery by direct injection with the efficiency of such delivery using the composition.

At selected times after wound dressing, wound healing morphology is examined, including, for example, immunohistochemical demonstration of wound healing protein expression and in situ hybridization experiments to demonstrate persistence of the expression construct in the cells of the excision wounded tissue.

The experimental procedures described in this Example can be used to demonstrate delivery of a virus vector to wounded tissue in an animal using a composition of the invention.

In one set of experiments performed according to these methods, a hydrogel matrix comprising a virus vector which comprised an expression construct encoding a β-galactosidase protein, as described herein in Example 1, was topically administered to excisional wounds made in rabbit ears. In both ischemic (N=4) and non-ischemic (N=4) excisional wounds, significant β-galactosidase expression was observed at cells located throughout the wounded tissue following administration of the hydrogel matrix to the wound by topical application of the matrix thereto. These results demonstrate that the compositions described herein can be used to deliver a virus vector to a wounded tissue.

EXAMPLE 5

The usefulness of a composition of the invention for delivering a virus vector to wounded tissue of an animal for the purpose of promoting wound healing can also be assessed using a rabbit ischemic injury model, as described (Zhao et al., 1994, Arch. Surgery 129:1043–1049; Pierce et al., 1991, Am. J. Pathol. 138:629–646). Compositions and virus vector formulations analogous to those described herein in Example 5 are used. Wound healing morphology, as described in Example 5, and the extent of re-vascularization of the wound site are assessed to determine the usefulness of the composition for delivering a virus vector to wounded tissue.

In one set of experiments performed according to these methods, a hydrogel matrix comprising a virus vector which comprised an expression construct encoding a β-galactosidase protein, as described herein in Example 1, was topically administered to ischemic rabbit ear wounds. The same amount of the virus vector (i.e. about $10^8$ plaque forming units was administered to identically-wounded rabbits by injection of a suspension of the vector at the site of the wound.

Figure 3A:
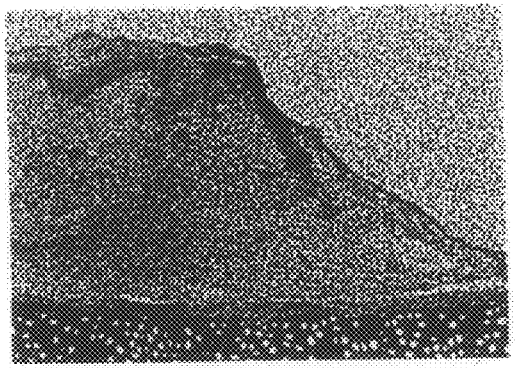
FIGS. 3A, 3B, and 3C, is a trio of images which demonstrate in vivo delivery of adenovirus vector to ischemic wounded rabbit ear tissue, as described herein.
Figure 3B:
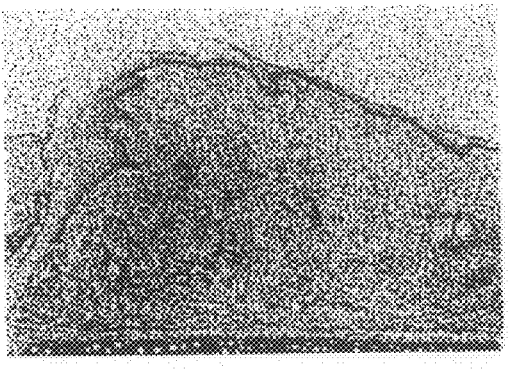
Figure 3C:
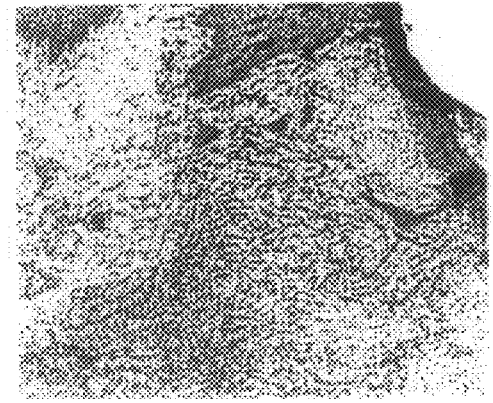

Two six millimeter excisional wounds were made in ischemic and non-ischemic New Zealand rabbit ears. Ischemic rabbit ears were performed by occlusion of an artery supplying the ear, using standard techniques. Greater β-galactosidase expression was observed in the wounds to which the hydrogel matrix was administered than in the wounds to which the virus vector was administered by injection, as is evident by comparing FIGS. 3A and 3C with FIG. 3B. After two weeks, β-galactosidase expression was still evident in wounded tissue to which the hydrogel matrix was administered, but there was less extensive in β-galactosidase expression detectable in wounded tissue to which the virus vector was administered by injection. Impairment of re-epithelialization of rabbit ear wounds, which was observed upon injection into wounded rabbit ear tissue of an adenovirus suspension similar to that here, was not observed using the hydrogel matrix composition described in this Example. These results demonstrate that the compositions described herein can be used to deliver a virus vector to a wounded tissue in a sustained-release manner. Furthermore, delivery of the virus vector using the hydrogel matrix reduced the inflammatory response induced by the presence of the adenovirus vector, as evidenced by the absence or reduction of re-epithelialization impairment observed using the hydrogel matrix, relative to direct injection of the vector.

EXAMPLE 6

The usefulness of a composition of the invention for delivering a virus vector to wounded tissue of an animal for the purpose of promoting wound healing can also be assessed using a rat intestinal anastomosis model as follows. Two-month-old rats are subjected to laparotomy, and the colon of each is incised and anastomosed. A wedge of mesenteric vessels is ligated to make the area of the anastomosis ischemic. Under these condition, a near uniform anastomotic breakdown and leak of the enteric contents occurs in non-treated animals.

The laporotomized rats are divided into three groups: one group is treated with a composition comprising a virus vector which comprises an expression construct encoding a wound healing protein such as PDGF-BB; a second group is treated with the same composition which does not comprise the virus vector; a third group is not treated. In treated rats, the composition is applied in the form of a bulk material applied around the outside of the anastomosis. After two weeks the animals in each of the three groups are sacrificed. For each group of rats, survival, anastomotic healing, presence or absence of peritonitis, intestinal lumen patency, tensiometry, and evidence of wound healing protein expression are assessed to determine the efficacy of the composition for delivering the virus vector to the wounded tissue.

EXAMPLE 7

The usefulness of a composition of the invention for delivering a virus vector to an animal in utero for the purpose of inducing immune tolerance of the virus vector in the animal or for delivering the virus vector to cells or a tissue of the animal can be assessed using the experimental procedures described in this Example.

The composition comprises a virus vector comprising a transfection indicator. The composition is delivered to a fetal sheep at 65 days gestation by injection into the fetal peritoneum using a 22 gauge needle. Placement of the needle into the peritoneum is guided using an ultrasound or similar non-invasive imaging device. For comparison, an amount of the same virus vector approximately equivalent to the amount of vector in the composition is injected into a separate fetal sheep in the form of a suspension of the vector in a physiologically acceptable carrier.

The sheep are carried to term, and a total body survey for the transfection indicator is performed. The total body survey can be performed by performing PCR or reverse transcriptase- PCR using appropriate primers to detect a nucleic acid transfection indicator, or the survey can be performed by performing Western blotting or activity assays (e.g. a β-galactosidase activity assay) to detect a protein transfection indicator. Identification of the presence of the transfection indicator at one or more body locations in the fill-term sheep is an indication that in utero administration of the virus vector effected transfection by the vector of cells at those body locations or their precursors.

The full-term sheep are also assayed for development of neutralizing antibodies to the virus vector or to a protein transfection indicator. These studies can be performed by administering either the virus vector or the protein transfection indicator to the sheep post-partum, and assessing whether an immune response is induced. The absence of induction of an immune response to post-partum administration of the virus vector or the protein transfection indicator is an indication that in utero administration of the virus vector induced immune tolerization of the virus vector or the protein transfection indicator.

EXAMPLE 8

In this Example an antibody-virus-cross-linked hydrogel composition comprising an adenovirus vector comprising a nucleic acid encoding bacterial beta-galactosidase was prepared and used to transfect cultured cells. The transfection of cells using this antibody-virus-cross-linked hydrogel composition was compared with the transfection of cells using a non-antibody-virus-cross-linked hydrogel composition.

The antibody-virus-cross-linked hydrogel composition was made as follows. The adenovirus vector was incubated for 30 minutes at 37° C. and pH 7.4 with a suspension of a biotinylated antibodies which bound specifically with the adenovirus vector. Biotinylated antibody-bound adenovirus vector particles were generated. A suspension of the biotinylated antibody-bound adenovirus vector particles was mixed with a suspension of collagen and an avidin, and the mixture was permitted to gel at 37° C. to yield the antibody-virus-cross-linked hydrogel composition. In this example, bovine type I collagen (Vitrogen, Collagen Corp., San Francisco, Calif.), and neutravidin (Pierce Chemical Co., Rockford, Ill.) were used. In the preparation, a 1:1 ratio of collagen to neutravidin was used, typically combining 10 milligrams of each, adding to this mixture $10^{10}$ plaque forming units of type 5 adenovirus (CMV promoter, replication defective) that was combined in a 1:1 ratio with 5 microliters of each of polyclonal goat-antihexon antiserum and adenovirus. The non-antibody-virus-cross-linked hydrogel composition was prepared similarly, except that virus vector particles which did not comprise bound antibody were used in place of biotinylated antibody-bound adenovirus vector particles. The antibody-virus-cross-linked hydrogel composition was significantly more rigid than the control (i.e. non-antibody-virus-cross-linked) hydrogel composition.

The antibody-virus-cross-linked and control hydrogel compositions were separately contacted with A10 cells in stationary culture dishes. Substantially all cells in culture dishes containing the control hydrogel composition expressed beta-galactosidase. In contrast, only cells which were close to the antibody-virus-cross-linked hydrogel composition expressed beta-galactosidase activity. These results demonstrate that antibody-virus-cross-linking of hydrogel compositions can modulate release of the (transfectious) virus vector in a biological environment.

EXAMPLE 9

In this Example, an adenovirus vector was bound with a collagen hydrogel matrix in a transfectious form by linking a biotinylated antibody to the collagen matrix by way of an avidin protein linked to the matrix. The avidin protein was linked to the matrix using a water soluble carbodiimide.

The composition in this Example was made as follows. Bovine type I collagen (Vitrogen™, Collagen Corp., San Francisco, Calif.) was suspended with an approximately equal amount of neutravidin (Pierce Chemical Co., Rockford, Ill.), and the two proteins were linked using a water soluble carbodiimide (1-ethyl-3-(3 dimethyl-aminopropyl)carbodiimide). The collagen and neutravidin formed a hydrogel which had robust mechanical properties at 37° C., owing at least in part to rigidity imparted to the hydrogel by cross-linking between collagen and neutravidin, between collagen molecules, and between neutravidin molecules. The collagen-neutravidin hydrogel was contacted with a suspension of biotinylated polyclonal antibodies which exhibited specific binding with an adenovirus gene vector. Antibody binding to the hydrogel was confirmed using a fluorescently-labeled antibody which bound specifically with the biotinylated antibodies.

Biotinylated antibody-bound collagen-neutravidin hydrogel was contacted with a suspension of an adenovirus vector comprising a nucleic acid encoding bacterial beta-galactosidase. Biotinylated antibody-bound collagen-neutravidin hydrogel which was not contacted with the adenovirus vector was used as a control hydrogel matrix. Hydrogel matrix having the virus vector bound thereto were next contacted with A10 cells in culture, and expression of beta-galactosidase in the cells was investigated about 72 hours after contacting the cells with the matrix. Cells which were adjacent the hydrogel matrix having the virus vector bound thereto expressed beta-galactosidase, but cells which were adjacent the control hydrogel matrix did not. These results demonstrate that virus vectors can be bound with a hydrogel matrix in a transfectious form using a virus binding agent comprising a protein-ligand pair and an antibody which binds specifically with the virus vector, wherein one member of the protein-ligand pair is linked to the matrix and the other member is linked to the antibody.

EXAMPLE 10

A hydrogel comprising bovine type I collagen and biotinylated anti-adenovirus antibody containing an adenovirus vector which comprised a reporter polynucleotide encoding green fluorescent protein and to which avidin was bound was provided to the myocardium of a post-natal pig by injecting or sewing a composition comprising the hydrogel therein. Extra-myocardial tissues of the pig were sampled, and the presence of the reporter gene could not be detected by PCR amplification (using reporter polynucleotide-specific primers) in those tissues seven days following administration of the hydrogel. Reporter gene expression was detected in myocardium These experiments demonstrate that the compositions and methods described herein can be used to deliver a virus vector in a transfectious form to a selected tissue in a mammal, and that such delivery results in highly localized vector delivery.

The disclosures of each and every patent, patent application, and publication cited herein are hereby incorporated herein by reference in their entirety.

While this invention has been disclosed with reference to specific embodiments, it is apparent that other embodiments and variations of this invention can be devised by others skilled in the art without departing from the true spirit and scope of the invention. The appended claims are intended to be construed to include all such embodiments and equivalent variations.

What is claimed is:

1. A composition for delivery of a virus vector to an animal cell by local administration, the composition comprising a hydrogel precursor mixture having the virus vector suspended therein, wherein a component of the hydrogel precursor mixture is bound with an antibody which binds specifically with the virus vector, and wherein the hydrogel precursor mixture stiffens at physiological temperature and at a physiological calcium level to form a hydrogel matrix containing the virus vector therein in a transfectious form.

2. The composition of claim 1, wherein the hydrogel matrix is biodegradable.

3. The composition of claim 2, wherein the hydrogel precursor mixture comprises a collagen.

4. The composition of claim 3, wherein the collagen is a type I collagen.

5. The composition of claim 4, wherein the type I collagen is bovine type I collagen.

6. The composition of claim 3, wherein the hydrogel precursor mixture further comprises a poloxamer.

7. The composition of claim 3, wherein the antibody is bound with the collagen.

8. The composition of claim 1, wherein the virus vector is selected from the group consisting of an adenovirus vector, a lentivirus vector, a retrovirus vector, an adeno-associated virus vector, and a herpesvirus vector.

9. The composition of claim 8, wherein the virus vector is an adenovirus vector.

10. The composition of claim 1, wherein the hydrogel precursor mixture further comprises a polycation.

11. The composition of claim 10, wherein the polycation is selected from the group consisting of polylysine, polyarginine, polyornithine, polyhistidine, myelin basic protein, a low molecular weight glycopeptide, a cationic amphiphilic alpha-helical oligopeptide having a repeating sequence, a histone, a galactosylated histone, polybrene, spermine, spermidine, prolamine, polyethylenimine, putrescine, cadaverine, and hexamine.

12. The composition of claim 11, wherein the polycation is poly-L-lysine.

13. The composition of claim 1, wherein the virus vector comprises a transfection indicator.

14. The composition of claim 1, wherein the virus vector comprises a nucleic acid selected from the group consisting of an expression construct encoding a wound healing therapeutic protein, an expression construct encoding an anti-restenotic protein, an expression construct encoding an anti-oncogenic protein, an anti-restenotic antisense oligonucleotide, and an anti-oncogenic antisense oligonucleotide.

15. The composition of claim 14, wherein the nucleic acid is an expression construct encoding a wound healing therapeutic protein selected from the group consisting of TGF-β, FGF, PDGF, PDGF-BB, IGF, M-CGF, BMP, GH, and PTH.

16. The composition of claim 14, wherein the nucleic acid is an expression construct encoding an anti-restenotic protein selected from the group consisting of TPA, TGF-β, FGF, Rb, p21, and TK.

17. The composition of claim 14, wherein the nucleic acid is an expression construct encoding an anti-oncogenic protein encoded by a gene selected from the group consisting of abl, akt2, apc, bcl2α, bcl2β, bcl3, bcr, brca1, brca2, cbl, ccnd1, cdk4, crk-II, csf1r/fms, dbl, dcc, dpc4/smad4, e-cad, e2f1/rbap, egfr/erbb-1, elk1, elk3, eph, erg, ets1, ets2, fer, fgr/src2, fli1/ergb2, fos, fps/fes, fra1, fra2, fyn, hck, hek, her2/erbb-2/neu, her3/erbb-3, her4/erbb-4, hras1, hst2, hstf1, ink4a, ink4b, int2/fgf3, jun, junb, jund, kip2, kit, kras2a, kras2b, lck, lyn, mas, max, mcc, met, mlh1, mos, msh2, msh3, msh6, myb, myba, mybb, myc, mycl1, mycn, nf1, nf2, nras, p53, pdgfb, pim1, pms1, pms2, ptc, pten, raf1, rb1, rel, ret, ros1, ski, src1, tal1, tgfbr2, thra1, thrb, tiam1, trk, vav, vhl, waf, wnt1, wnt2, wt1, and yes1.

18. The composition of claim 14, wherein the nucleic acid is an anti-restenotic antisense oligonucleotide selected from the group consisting of a c-myb antisense oligonucleotide, a c-myc antisense oligonucleotide, and a PCNA antisense oligonucleotide.

19. The composition of claim 14, wherein the nucleic acid is an anti-oncogenic antisense oligonucleotide selected from the group consisting of an abl antisense oligonucleotide, an akt2 antisense oligonucleotide, an apc antisense oligonucleotide, a bcl2α antisense oligonucleotide, a bcl2β antisense oligonucleotide, a bcl3 antisense oligonucleotide, a bcr antisense oligonucleotide, a brca1 antisense oligonucleotide, a brca2 antisense oligonucleotide, a cbl antisense oligonucleotide, a ccnd1 antisense oligonucleotide, a cdk4 antisense oligonucleotide, a crk-II antisense oligonucleotide, a csf1r/fms antisense oligonucleotide, a dbl antisense oligonucleotide, a dcc antisense oligonucleotide, a dpc4/smad4 antisense oligonucleotide, an e-cad antisense oligonucleotide, an e2f1/rbap antisense oligonucleotide, an egfr/erbb-1 antisense oligonucleotide, an elk1 antisense oligonucleotide, an elk3 antisense oligonucleotide, an eph antisense oligonucleotide, an erg antisense oligonucleotide, an ets1 antisense oligonucleotide, an ets2 antisense oligonucleotide, an fer antisense oligonucleotide, an fgr/src2 antisense oligonucleotide, an fli1/ergb2 antisense oligonucleotide, an fos antisense oligonucleotide, an fps/fes antisense oligonucleotide, an fra1 antisense oligonucleotide, an fra2 antisense oligonucleotide, an fyn antisense oligonucleotide, an hck antisense oligonucleotide, an hek antisense oligonucleotide, an her2/erbb-2/neu antisense oligonucleotide, an her3/erbb-3 antisense oligonucleotide, an her4/erbb-4 antisense oligonucleotide, an hras1 antisense oligonucleotide, an hst2 antisense oligonucleotide, an hstf1 antisense oligonucleotide, an ink4a antisense oligonucleotide, an ink4b antisense oligonucleotide, an int2/fgf3 antisense oligonucleotide, a jun antisense oligonucleotide, a junb antisense oligonucleotide, a jund antisense oligonucleotide, a kip2 antisense oligonucleotide, a kit antisense oligonucleotide, a kras2a antisense oligonucleotide, a kras2b antisense oligonucleotide, an lck antisense oligonucleotide, an lyn antisense oligonucleotide, an mas antisense oligonucleotide, an max antisense oligonucleotide, an mcc antisense oligonucleotide, an met antisense oligonucleotide, an mlh1 antisense oligonucleotide, an mos antisense oligonucleotide, an msh2 antisense oligonucleotide, an msh3 antisense oligonucleotide, an msh6 antisense oligonucleotide, an myb antisense oligonucleotide, an myba antisense oligonucleotide, an mybb antisense oligonucleotide, an myc antisense oligonucleotide, an mycl1 antisense oligonucleotide, an mycn antisense oligonucleotide, an nf1 antisense oligonucleotide, an nf2 antisense oligonucleotide, an nras antisense oligonucleotide, a p53 antisense oligonucleotide, a pdgfb antisense oligonucleotide, a pim1 antisense oligonucleotide, a pms1 antisense oligonucleotide, a pms2 antisense oligonucleotide, a ptc antisense oligonucleotide, a pten antisense oligonucleotide, an raf1 antisense oligonucleotide, a rb1 antisense oligonucleotide, an rel antisense oligonucleotide, an ret antisense oligonucleotide, an ros1 antisense oligonucleotide, an ski antisense oligonucleotide, an src1 antisense oligonucleotide, a tal1 antisense oligonucleotide, a tgfbr2 antisense oligonucleotide, a thra1 antisense oligonucleotide, a thrb antisense oligonucleotide, a tiam1 antisense oligonucleotide, a trk antisense oligonucleotide, a vav antisense oligonucleotide, a vhl antisense oligonucleotide, a waf1 antisense oligonucleotide, a wnt1 antisense oligonucleotide, a wnt2 antisense oligonucleotide, a wt1 antisense oligonucleotide, and a yes1 antisense oligonucleotide.

20. The composition of claim 1, wherein the antibody is covalently bound with the component of the hydrogel precursor mixture.

21. The composition of claim 1, wherein the antibody is covalently bound with biotin and wherein the component of the hydrogel precursor rnixture is covalently bound with an avidin.

22. The composition of claim 21, wherein the avidin is streptavidin.

23. The composition of claim 1, wherein the hydrogel precursor mixture comprises a poloxamer.

24. An implantable device having a surface coated with a hydrogel matrix containing a virus vector therein in a transfectious form, wherein the hydrogel matrix is bound with an antibody which binds specifically with the virus vector.

25. The implantable device of claim 24, wherein the implantable device comprises a wound dressing.

26. The implantable device of claim 24, wherein the implantable device comprises a suture.

27. The implantable device of claim 24, wherein the implantable device comprises a particle.

28. The implantable device of claim 24, wherein the implantable device comprises a vascular stent.

29. The implantable device of claim 24, wherein the implantable device comprises an endotracheal tube.

30. A method of making a composition for delivery, of a virus vector to an animal tissue, the method comprising administering to a body location in fluid communication with the tissue a hydrogel precursor mixture having the virus vector suspended therein, wherein a component of the hydrogel precursor mixture is bound with an antibody which binds specifically with the virus vector, whereby the hydrogel precursor mixture stiffens upon administration to the body location to form a hydrogel matrix containing the virus vector therein in a transfectious form.

31. A method of making a composition for delivery of a virus vector to an animal cell, the method comprising contacting the cell with a hydrogel precursor composition which comprises a collagen bound with an antibody which binds specifically with the virus vector, a poloxamer, and the virus vector at physiological temperature and at a physiological concentration of a polyvalent cation, whereby the hydrogel precursor mixture stiffens to form a hydrogel matrix containing the virus vector therein in a transfectious form.

32. A method of delivering a virus vector to an animal tissue, the method comprising administering to a body location in fluid communication with the animal tissue a hydrogel precursor mixture having the virus vector suspended therein, wherein a component of the hydrogel precursor mixture is bound with an antibody which binds specifically with the virus vector, whereby the hydrogel precursor mixture stiffens upon administration to the body location to form a hydrogel matrix containing the virus vector therein in a transfectious form.

33. A method of delivering a virus vector to an animal cell, the method comprising placing in fluid communication with the cell a composition comprising a hydrogel matrix having the virus vector contained therein in a transfectious form, wherein a component of the hydrogel precursor mixture is bound with an antibody which binds specifically with the virus vector.

34. A kit comprising a collagen bound with an antibody which binds specifically with a virus vector, a poloxamer, and an instructional material which describes a method of making a collagen hydrogel matrix which comprises the poloxamer and which contains the virus vector therein in a transfectious form.

* * * * *